US012642786B2

(12) United States Patent
Kim et al.

(10) Patent No.: US 12,642,786 B2
(45) Date of Patent: Jun. 2, 2026

(54) METHODS, COMPOSITIONS AND KITS FOR TREATING MULTIPLE SCLEROSIS AND OTHER DISORDERS

(71) Applicant: The Johns Hopkins University, Baltimore, MD (US)

(72) Inventors: Paul M. Kim, Baltimore, MD (US); Michael D. Kornberg, Baltimore, MD (US); Peter A. Calabresi, Baltimore, MD (US); Solomon H. Snyder, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 780 days.

(21) Appl. No.: 17/311,684

(22) PCT Filed: Dec. 6, 2019

(86) PCT No.: PCT/US2019/065109
§ 371 (c)(1),
(2) Date: Jun. 7, 2021

(87) PCT Pub. No.: WO2020/118282
PCT Pub. Date: Jun. 11, 2020

(65) Prior Publication Data

US 2022/0023255 A1 Jan. 27, 2022

Related U.S. Application Data

(60) Provisional application No. 62/776,776, filed on Dec. 7, 2018.

(51) Int. Cl.
*A61K 31/366* (2006.01)
*A61P 25/00* (2006.01)

(52) U.S. Cl.
CPC ............ *A61K 31/366* (2013.01); *A61P 25/00* (2018.01)

(58) Field of Classification Search
CPC .............................. A61K 31/666; A61P 25/00
See application file for complete search history.

(56) References Cited

U.S. PATENT DOCUMENTS 5,145,842 A 9/1992 Driedger et al.
2010/0022645 A1 1/2010 Nelson et al.
(Continued)

FOREIGN PATENT DOCUMENTS

WO 2014117021 A2 7/2014
WO WO-2017062924 A1 * 4/2017 ........... A61K 31/365

OTHER PUBLICATIONS

Kornberg et al.; "Bryostatin-1 alleviated experimental multiple sclerosis"; Feb. 12, 2018; PNAS; 115(9): 2186-2191 (Year: 2018).*
(Continued)

*Primary Examiner* — Timothy P Thomas
(74) *Attorney, Agent, or Firm* — Fox Rothschild LLP; Peter F. Corless

(57) ABSTRACT

The disclosure provides methods for (i) treating multiple sclerosis in patient, (ii) treating a patient having symptoms of multiple sclerosis, (iii) preventing the onset of multiple sclerosis symptoms in patient having multiple sclerosis or predisposed to multiple sclerosis; (iv) promoting or enhancing immunomodulation and remyelination and/or myelin repair in a subject in need thereof; (v) a neuroinflammatory disorder; (vi) Amyotrophic Lateral Sclerosis; or (vii) a demyelinating disease or disorder or a hypomyelinating condition, each method comprising administering a therapeutically effective amount of a bryostatin compound to the patient.

10 Claims, 16 Drawing Sheets

(56) References Cited

U.S. PATENT DOCUMENTS

| | | | |
|---|---|---|---|
| 2016/0082015 | A1 | 3/2016 | Rubin |
| 2018/0000771 | A1 | 1/2018 | Inoue et al. |

OTHER PUBLICATIONS

Sun et al., "Synergistic Effects of Chronic Bryostatin-1 and alpha-tocopherol on spatial learning and memory in rats," European Journal of Pharmacology, 584:2-3, pp. 328-337, 2008.

Kornberg et al., "Bryostatin-1 Alleviates Experimental Multiple Sclerosis," Proceedings of the National Academy of Sciences of the United States of American, 115:9, pp. 2186-2191, 2018.

Safaeinejad et al., "Inhibition of Inflammation, Suppression of Matrix Metalloproteinases, Induction of Neurogenesis, and Anti-oxidant Property Make Bryostatin-1 a Therapeutic Choice for Multiple Sclerosis," Frontiers in Pharmacology, 9:625, pp. 1, 3.

Sun et al., "Synergistic Effects of Chronic Bryostatin-1 and alpha-tocopherol on spatial learing and memory in rates," European Journal of Pharmacology, 584:2-3, pp. 328-337, 2008.

International Search Report and the Written Opinion dated Feb. 26, 2020 from Corresponding PCT Application No. PCT/US2019/065109, pp. 1-11.

* cited by examiner

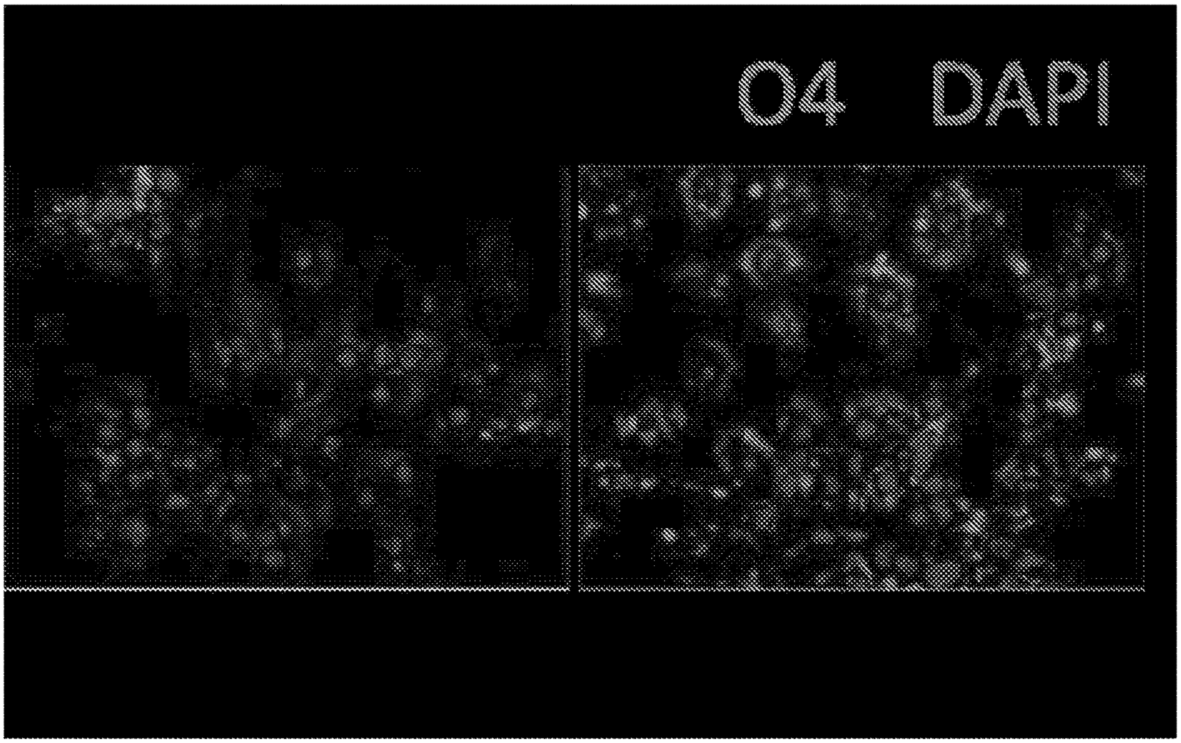
FIG. 5
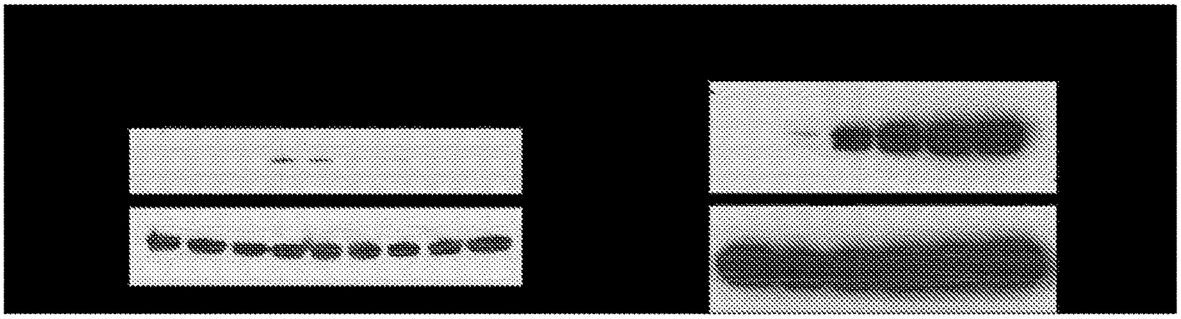
FIG. 6A
FIG. 6B

METHODS, COMPOSITIONS AND KITS FOR TREATING MULTIPLE SCLEROSIS AND OTHER DISORDERS

CROSS-REFERENCE TO RELATED APPLICATIONS

This application is a National Stage Application filed under 35 U.S.C. § 371, of International Patent Application No PCT/US2019/065109, filed on Dec. 6, 2019, which claims the benefit of and priority to U.S. Provisional Application No. 62/776,776, filed on Dec. 7, 2018. The entire contents of each of these application are incorporated herein by reference in their entirety.

GOVERNMENT RIGHTS

This invention was made with government support under grants NS041435 and MH018501 awarded by the National Institutes of Health. The government has certain rights in the invention.

TECHNICAL FIELD

In one aspect, this disclosure relates to methods for treating multiple sclerosis. In additional aspects, methods are provided for promoting or enhancing immunomodulation and remyelination and/or myelin repair in a subject in need thereof. In yet additional aspects, methods are provided for treating a neuroinflammatory disorder; Amyotrophic Lateral Sclerosis; or a demyelinating disease or disorder or a hypomyelinating condition.

BACKGROUND

Bryostatin-1 (bryo-1) is a naturally occurring macrocyclic lactone obtained from the marine bryozoan Bugula neritina. It has shown clinical promise in cancer and Alzheimer's disease models based on its actions on protein kinase C and has proceeded through phase 2 clinical trials in humans with a favorable safety profile.

Multiple sclerosis (MS) is an inflammatory disease of the central nervous system (CNS) that primarily targets oligodendrocytes and causes demyelination, although neurodegeneration is also a feature of the disease, particularly in its late stages. In most patients, early disease is characterized by acute episodes of focal inflammation causing neurologic disability, with intervening remission and at least partial recovery (termed relapsing-remitting MS (RRMS)). Subsequently, many patients with RRMS enter secondary progressive MS, which is characterized by progressive neurologic disability despite a lack of episodic relapses. Some patients initially present with primary progressive MS and have a progressive course from the beginning with no history of episodic relapse. Although the most substantial disability develops during progressive MS, progressive forms of the disease have proven most difficult to treat, representing a major unmet need for patients with MS. Furthermore, cognitive deficits are common and often debilitating in MS, particularly in progressive phases of disease, yet no treatments targeting these deficits are available.

It would be desirable to have new therapies for treating multiple sclerosis.

SUMMARY

In some aspects, the disclosure provides methods for treating multiple sclerosis in patient, comprising administering a therapeutically effective amount of a bryostatin to the patient.

In other aspects, the disclosure provides methods for treating a patient having symptoms of multiple sclerosis, comprising administering a therapeutically effective amount of a bryostatin to the patient.

In further aspects, the disclosure provides methods for preventing the onset of multiple sclerosis symptoms in patient having multiple sclerosis or predisposed to multiple sclerosis, comprising administering a therapeutically effective amount of a bryostatin to the patient.

In additional aspects, methods are provided for treating a patient suffering from a neuroinflammatory disorder, such as transverse myelitis (TM), optic neuritis, neuromyelitis optica (NMO), neuromyelitis optica spectrum disorder and sarcoidosis as well as multiple sclerosis. Such methods include administering to a patient in need thereof, (such as a patient identified as suffering from a neuroinflammatory disorder) an effective amount of one or more bryostatin compounds.

In another aspect, methods are provided for treating a subject suffering from Amyotrophic Lateral Sclerosis (ALS), comprising administering a therapeutically effective amount of a bryostatin to the subject. The subject may be identified as suffering from Amyotrophic Lateral Sclerosis and a bryostatin compound administered to the identified subject.

In yet additional aspects, methods are provided treating a patient suffering from demyelinating or a hypomyelinating condition, such as acute disseminated encephalomyelitis, periventricular leukomalacia, periventricular white matter injury, Tabes *Dorsalis*, Devic's disease, optic neuritis, progressive multifocal leukoencephalopathy, transverse myelitis, chronic inflammatory demyelinating polyneuropathy, anti-MAG peripheral neuropathy, adrenoleukodystrophy, adrenomyeloneuropathy, Guillain-Barre Syndrome, central pontine myelinolysis, diffuse white matter injury, inherited demyelinating diseases such as leukodystrophy, and/or Charcot Marie Tooth Disease. Such methods include administering to a subject in need thereof, (such as a patient identified as suffering from a demyelinating or a hypomyelinating disease or disorder) an effective amount of one or more bryostatin compounds.

In additional aspects, methods are provided for promoting or enhancing immunomodulation and remyelination and/or myelin repair in a subject in need thereof, which comprise administering to the subject an effective amount of one or more bryostatin compounds.

In yet other aspects, the bryostatin is bryostatin-1 of the structure:

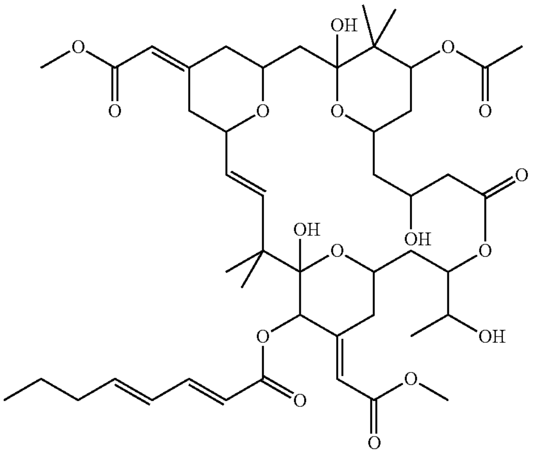

(bryostatin-1)

or a derivative, salt, or prodrug thereof.

In particular aspects, a subject will be identified and selected for treatment of a disease or disorder as disclosed herein, and then a bryostatin compound such as bryostatin-1 will be administered to the identified and selected subject.

For instance, a patient may be identified and selected as suffering from multiple sclerosis and that patient identified as suffering from multiple sclerosis may be administered a bryostatin compound such as bryostatin-1 to thereby alleviate or treat the multiple sclerosis.

In certain aspects, the present therapeutic methods are not associated with treatment of a subject suffering from Alzheimer's disease and/or cancer. In this aspect, subjects that are suffering from Alzheimer's disease and/or cancer and/or are seeking treatment for Alzheimer's disease and/or cancer would be excluded from the present therapeutic methods.

In a further aspect, pharmaceutical compositions are provided comprising a bryostatin compound such as bryostatin-1 optionally together with one or more additional, distinct agents for treatment of multiple sclerosis. For example, the additional agent may be ocrelizumab (Ocrevus), natalizurnab (Tysabri) and/or glairmar. The compositions suitably may comprise one or more pharmaceutically acceptable carriers.

In a further aspect, pharmaceutical compositions are provided comprising a bryostatin compound such as bryostatin-1 optionally together with one or more additional, distinct agents for treatment of a neuroinflammatory disorder or a demyelinating disorder or disease. For example, the additional agent may be ocrelizumab (Ocrevus), natalizumab (Tysabri), giatirmar, dimethyl fumerate (BG-12), fingolimod (FTY720), interferon beta-lb and/or mitoxantrone. The compositions suitably may comprise one or more pharmaceutically acceptable carriers.

In certain aspects, one or more bryostatin compounds are the sole therapeutic agents administered to a subject as a treatment for a particular indication. For example, one or more bryostatin compounds may be the sole agents administered to subject to treat multiple sclerosis, or a other neuroinflammatory disease or demyelinating disease or disorder for a given period such as 1, 2, 3, 4, 5, 6, or 7 days.

In a yet further aspect, kits are provided for use to treat multiple sclerosis as disclosed herein. Kits of the invention suitably may comprise 1) one or more bryostatin compounds such as bryostatin-1; and 2) instructions for using the one or more bryostatin compounds for treating multiple sclerosis disclosed herein. Preferably, a kit will comprise a therapeutically effective amount of one or more one or more bryostatin compounds such as bryostatin-1. The instructions suitably may be in written form, including as a product label.

In still further aspects, kits are provided for use to treat neuroinflammatory disorder or a demyelinating disorder or disease as disclosed herein. Kits of the invention suitably may comprise 1) one or more bryostatin compounds such as bryostatin-1; and 2) instructions for using the one or more bryostatin compounds for treating neuroinflammatory disorder or a demyelinating disorder or disease disclosed herein. Preferably, a kit will comprise a therapeutically effective amount of one or more one or more bryostatin compounds such as bryostatin-1. The instructions suitably may be in written form, including as a product label.

Other aspects of the invention are disclosed infra.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compounds, methods, and compositions disclosed. In addition, the drawings are not necessarily drawn to scale.

FIG. 1B are bar graphs showing the total numbers of $CD4^+$ ($CD3^+$; $CD4^+$), Th1 ($CD4^+$; $IFN\gamma^+$), and Th17 ($CD4^+$; $IL17^+$) lymphocytes. FIG. 1C are bar graphs showing the proportion of Th1 and Th17 cells among $CD4^+$ lymphocytes, with representative flow plots.

Curves were compared both before and after discontinuation-associated worsening (*P<0.05; **P<0.01).

Figure 3A:
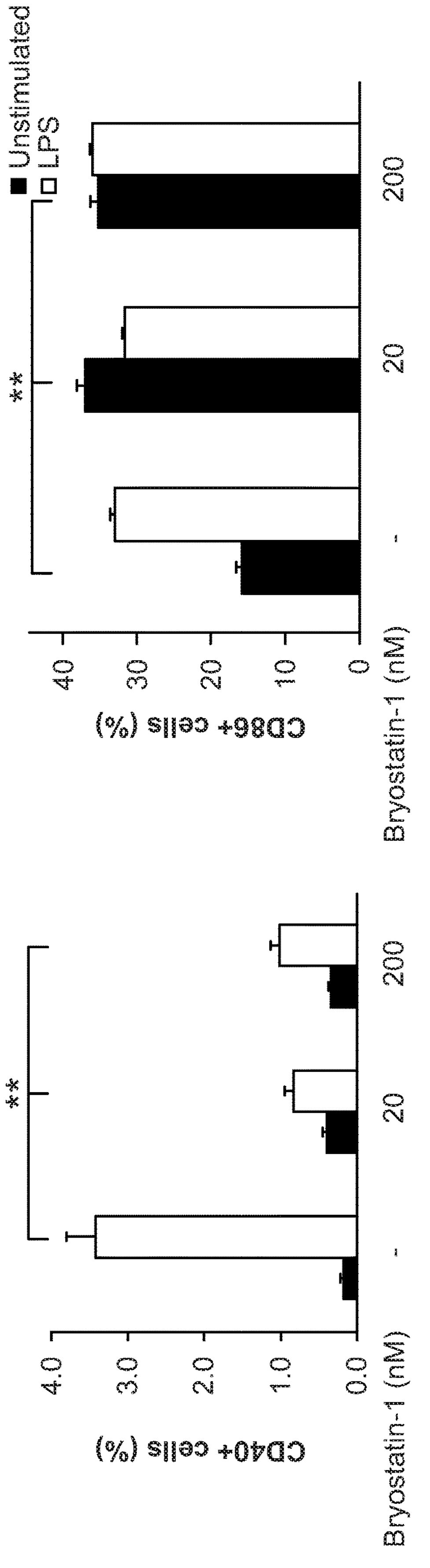
Figure 3B:
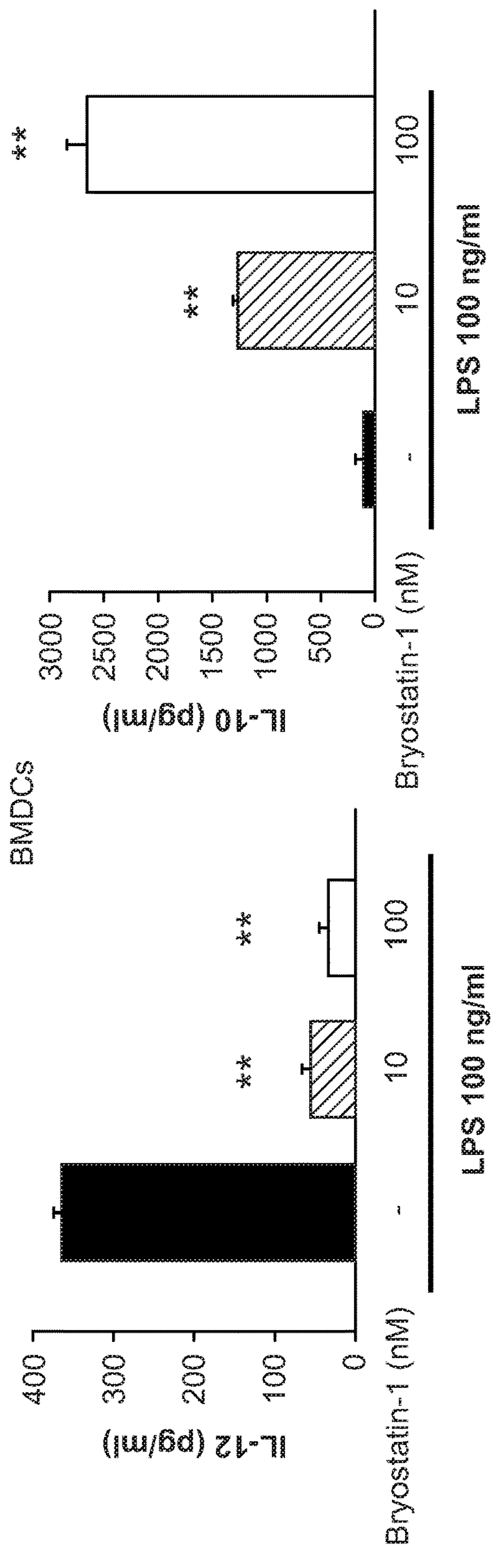
Figure 3C:
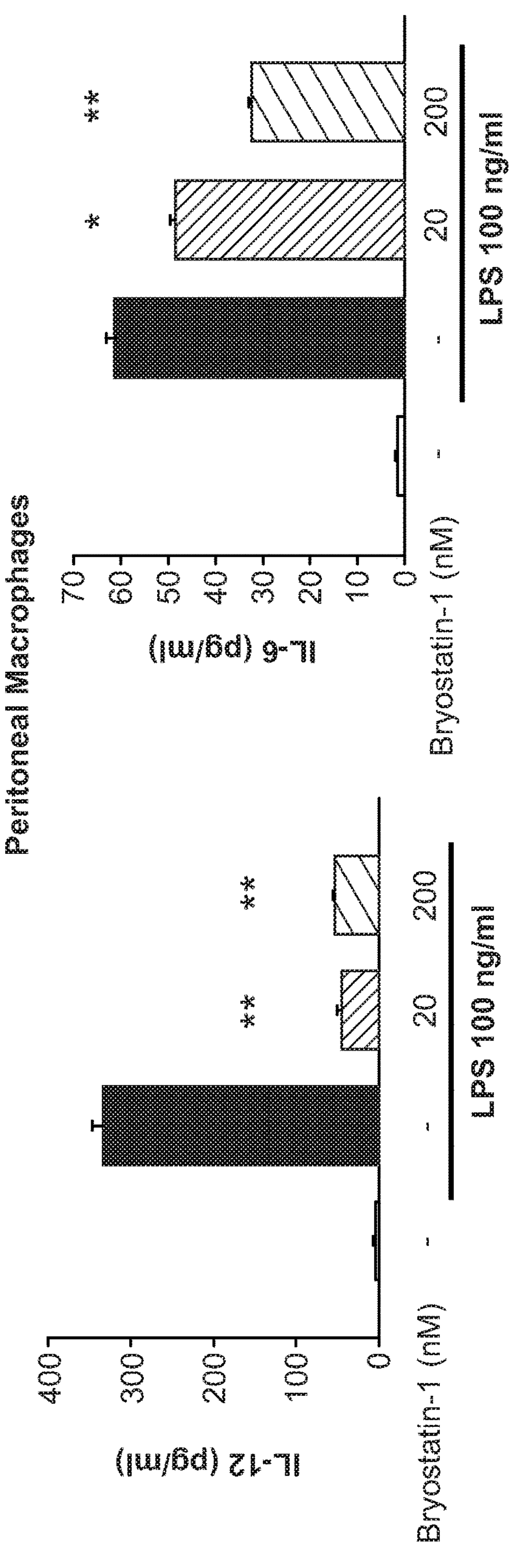
Figure 3D:
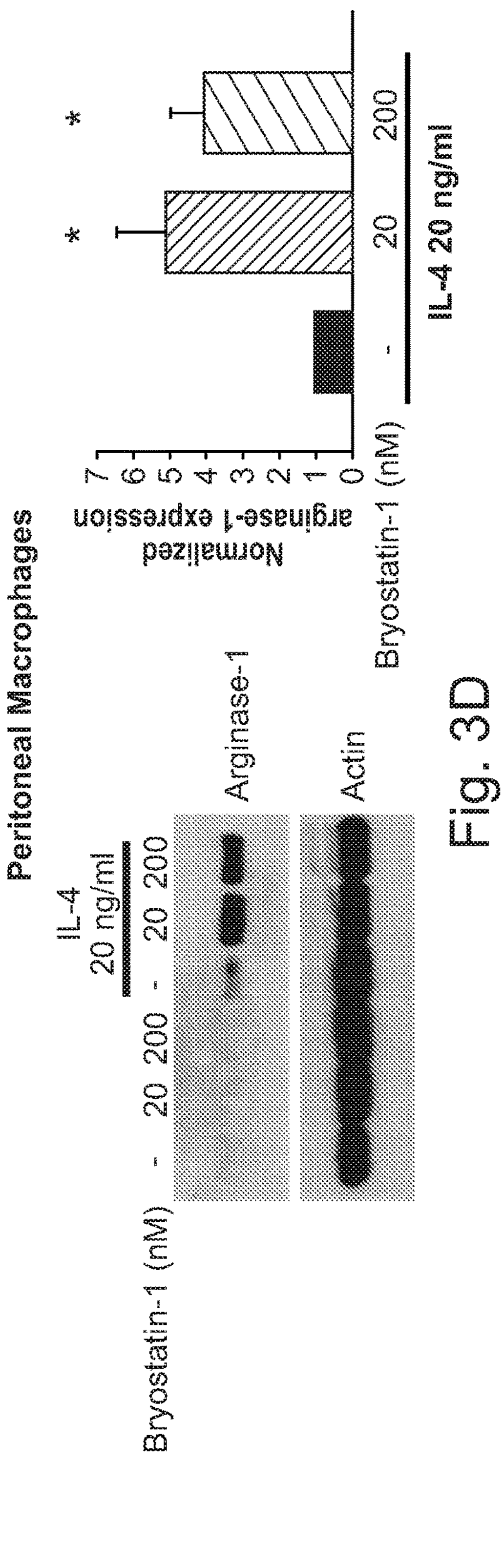

FIG. 3A are bar graphs of bone marrow-derived dendritic cells (BMDCs) that were treated overnight with the indicated doses of bryo-1, in the presence or absence of lipopolysaccharide (LPS; 100 ng/mL). Expression of CD40 and CD86 was then determined by flow cytometry; n=3 samples. FIG. 3B are bar graphs of BMDCs that were co-treated overnight with LPS and the indicated doses of bryo-1, and secretion of IL-12 and IL-10 into the culture media was measured via enzyme-linked immunosorbent assay (ELISA); n=2 experiments performed in replicates of 4. FIG. 3C are bar graphs of murine peritoneal macrophages (mPMs) that were co-treated overnight with LPS and the indicated doses of bryo-1, and secretion of IL-12 and IL-6 was measured via ELISA; n=2 experiments performed in replicates of 4. FIG. 3D (right) is a bar graph showing quantitation of arginase-1 Western blots from n=3 experiments for mPMs that were treated with the indicated doses of bryo-1 overnight in the presence or absence of IL-4 (20 ng/mL), and the expression of arginase-1 was assessed by Western blot. FIG. 3D (left) is a representative Western blot. All error bars represent SEM. Statistical analysis was performed using two-tailed Student's t test (*P<0.05; **P<0.01).

Figure 4A:
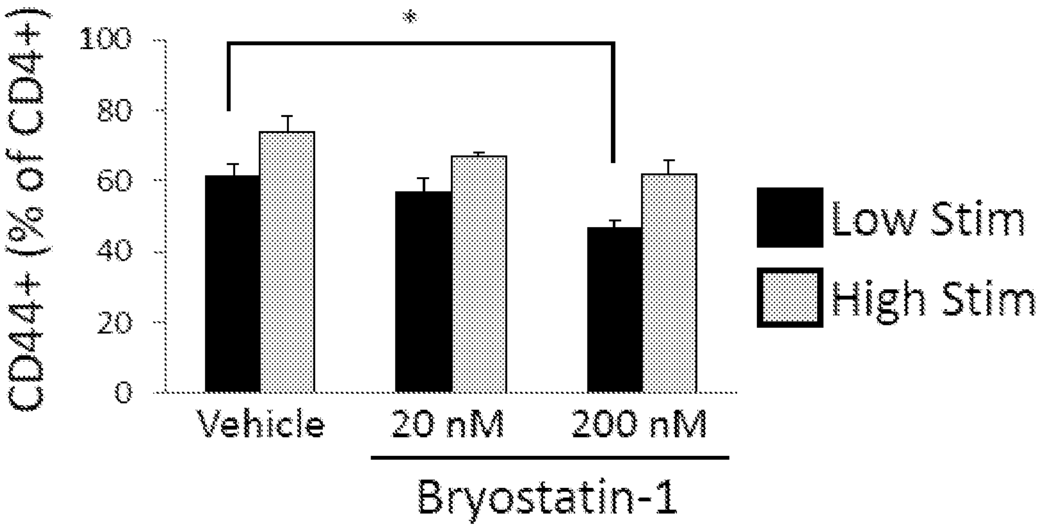
Figure 4B:
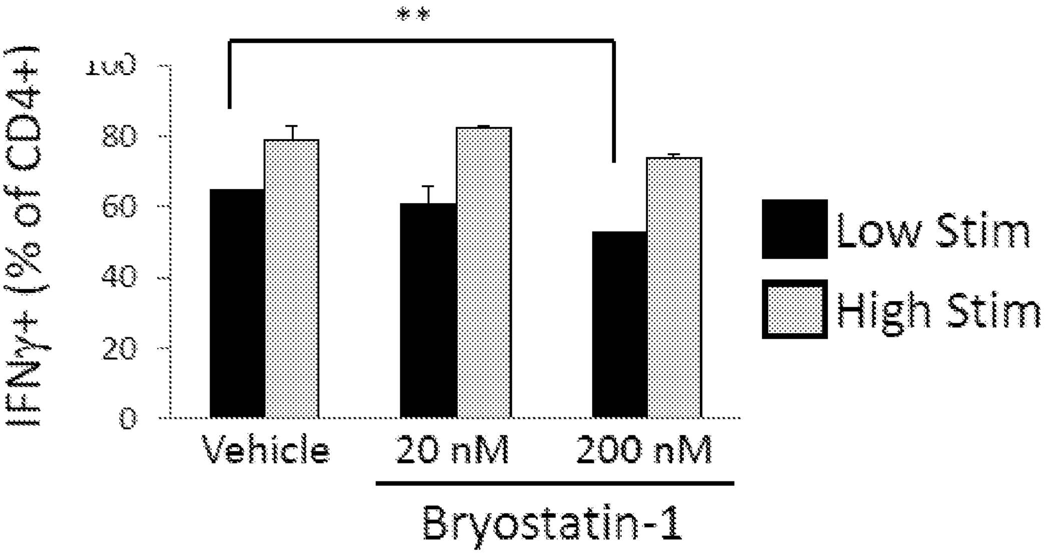
Figure 4C:
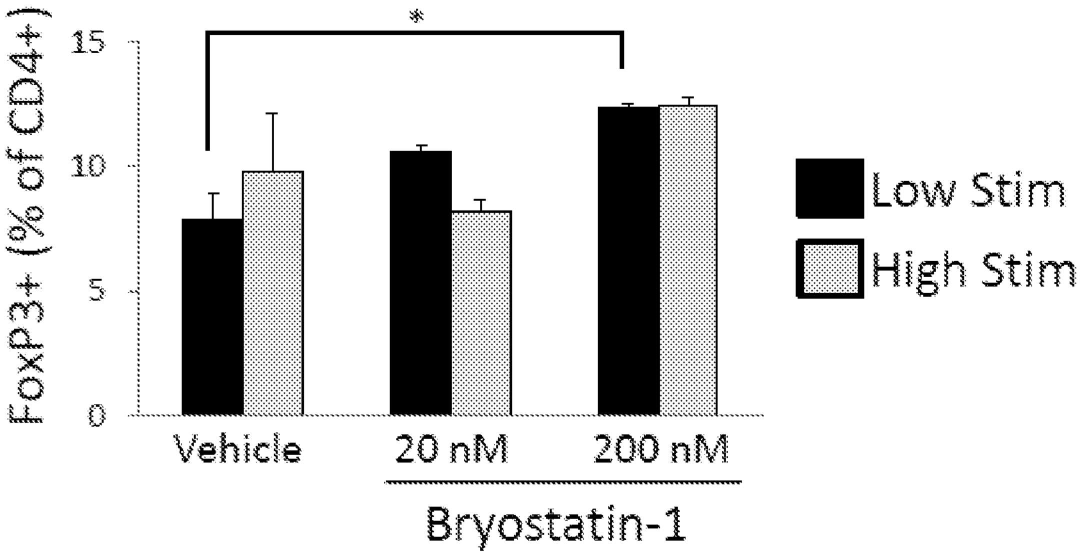

FIGS. 4A-4C are bar graphs showing the direct effects of bryo-1 on $CD4^+$ T-cells. Naive $CD4^+$ lymphocytes isolated by negative selection from mouse spleen were stimulated for 3 d with 0.25 μg/mL (low stim) or 1 μg/mL (high stim) each of α-CD3 and α-CD28 antibodies, along with the indicated concentrations of bryo-1. The percentages of $CD4^+$ lymphocytes expressing CD44 (FIG. 4A), IFNγ (FIG. 5B), and FoxP3 (FIG. 4C) were then determined by flow cytometry. All error bars represent SEM. Statistical analysis was performed using two-tailed Student's t test (*P<0.05; **P<0.01).

FIG. 5 shows representative images where cultured neurospheres were treated with 20 nM bryo-1 on alternating days for 1 week, followed by staining for 04.

FIG. 6 (includes FIGS. 6A and 6B) shows the immunoblot results of Example 8 which follows.

Figure 7:
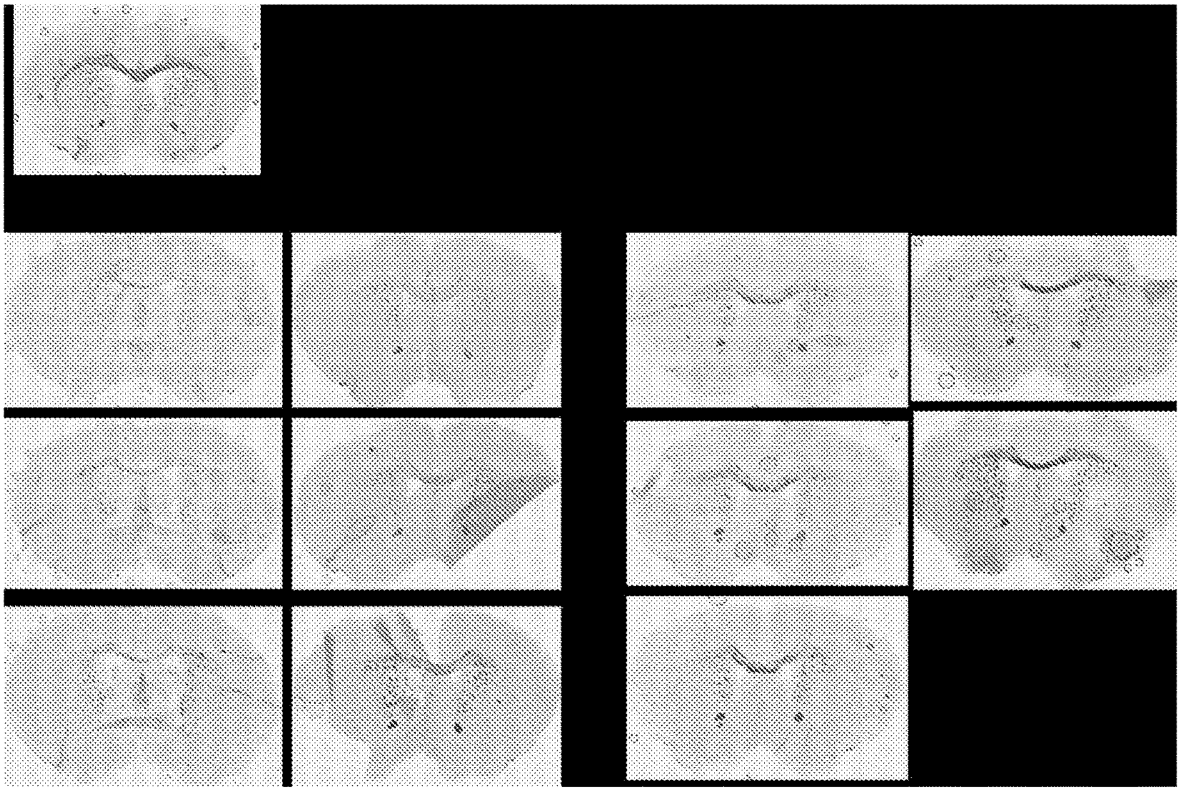

FIG. 7 shows the in vivo results of Example 9 which follows.

Figure 8:
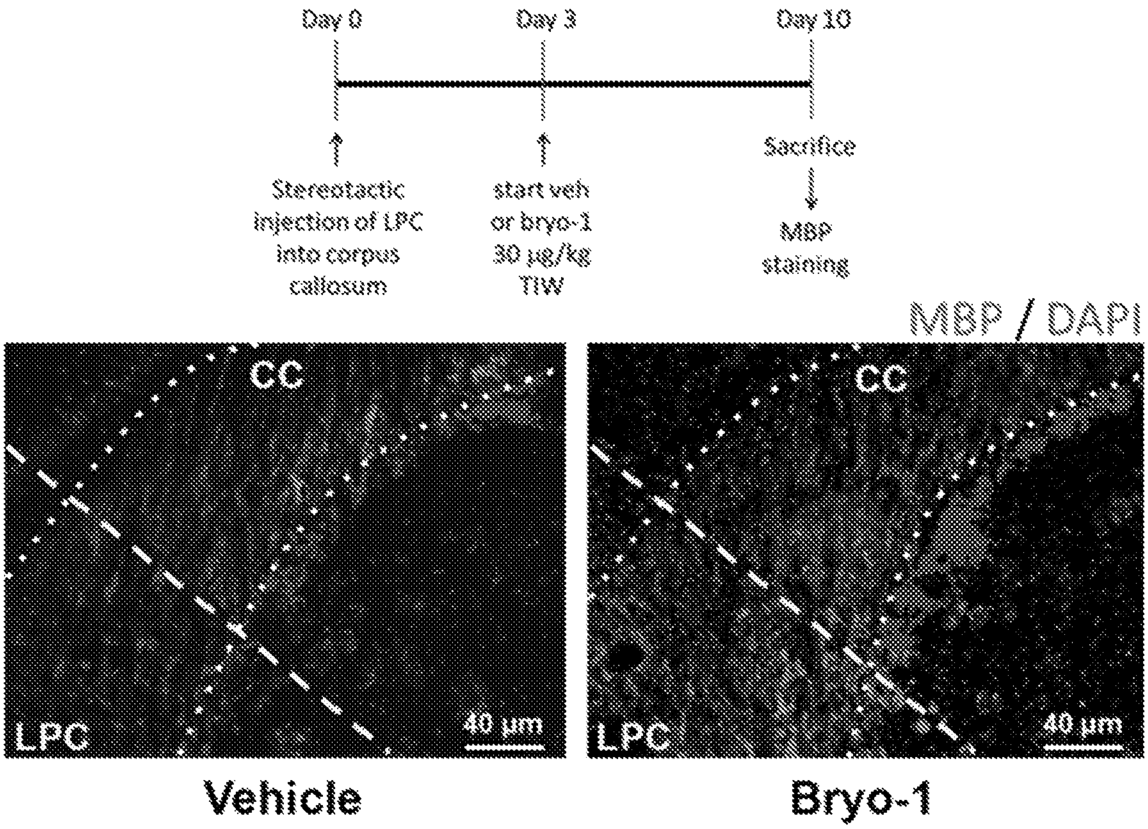

FIG. 8 shows results of Example 10 which follows where treatment with bryo-1 augments oligodendrogenesis after stereotactic LPC demyelination.

DETAILED DESCRIPTION OF ILLUSTRATIVE EMBODIMENTS

In searching for alternate MS therapies, the inventors found that bryostatins show great promise in treating multiple sclerosis. Specifically, the bryostatins showed preventative treatment of the onset of symptoms of multiple sclerosis; they abolish the onset of neurologic deficits in mice. Thus, the bryostatins may be used in treating relapsing forms of MS.

The inventors also found that bryostatins can promote an anti-inflammatory response, which is the opposite of how bryostatins work in cancer and Alzheimer's models. Although direct effects of bryostatins on T cells were observed, the most potent effects were on immune cells of myeloid lineage such as dendritic cells, macrophages, and microglia. Fascinatingly, the bryostatins are also believed to reverse neurologic deficits after multiple sclerosis onset, even when treatment is initiated at a late stage of disease when peak adaptive immunity has subsided. Thus, the bryostatins may be effective in treating multiple stages of multiple sclerosis across varying spectrums of severity, including progressive forms of MS for which treatment options are currently lacking.

In addition to this immunomodulatory effect on myeloid cells, we also have demonstrated in both in vitro and in vivo systems that a bryostatin compound including bryostatin-1 (bryo-1) can promote remyelination/repair both through direct effects on oligodendrocyte precursor cells and through promotion of a favorable CNS innate immune environment. Treatments promoting remyelination/repair are currently lacking and represent a major unmet need for MS patients.

In the disclosure, the singular forms "a,", "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude an optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

As discussed, the present disclosure provides methods for treating multiple sclerosis in patient, comprising administering a therapeutically effective amount of a bryostatin to the patient.

The terms "subject" and "patient" are used interchangeably and typically refer to mammals. In some embodiments, the patient or subject is a human. In other embodiments, the patient or subject is a veterinary or farm animal, a domestic animal or pet, or animal used for conducting clinical research.

"Treating" or variations thereof refers to eliminating, ameliorating, or reducing at least one neurological parameter of the disease or disorder. In some embodiments, treating refers to curing a patient of multiple sclerosis. In other embodiments, treating refers to ameliorating one or more symptom of multiple sclerosis in a patient. In still other embodiments, treating refers to eliminating one or more symptom of multiple sclerosis in a patient. In further embodiments, treating refers to reducing the progression of multiple sclerosis in a patient. In other embodiments, treating refers to preventing progress of multiple sclerosis in a patient. In yet other embodiments, treating refers to maintaining the stage of multiple sclerosis of a patient.

The term "multiple sclerosis", i.e., MS, as used herein refers to a chronic neuroinflammatory disease involving damage to the central nervous system (CNS), including, without limitation, damage to the sheaths of nerve cells in the brain and spinal cord. Thus, in certain embodiments, the bryostatin may repair some or all of the CNS damage using the methods described herein. In some embodiments, the multiple sclerosis is relapsing-remitting MS, secondary-progressive MS, primary-progressive MS, or progressive-relapsing MS. In other embodiments, the multiple sclerosis is relapsing-remitting MS or secondary-progressive MS. In further embodiments, the multiple sclerosis is secondary-progressive MS.

The term "bryostatin" as used herein refers to a chemical compound that is a macrolide lactone and suitably having the general structure of bryostatin-1. Thus, the term bryostatin also includes derivatives, salts, or prodrugs of bryostatin-1. In some embodiments, the methods described herein use a bryostatin derivative. In other embodiments, the methods described herein use a bryostatin salt. In further embodiments, the methods described herein use a bryostatin prodrug. In yet further embodiments, the methods described herein use bryostatin-1.

The general structure of byrostatin-1 is of one of formula (I)-(X), wherein ∿∿ refers point of the molecule that is substituted with a substituent as described herein:

(I)

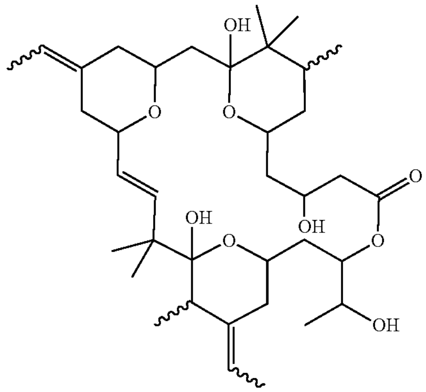

-continued (II)

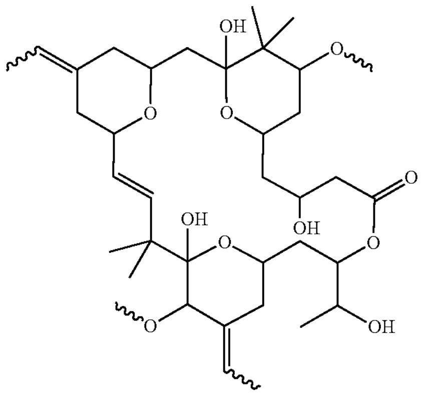

(III)

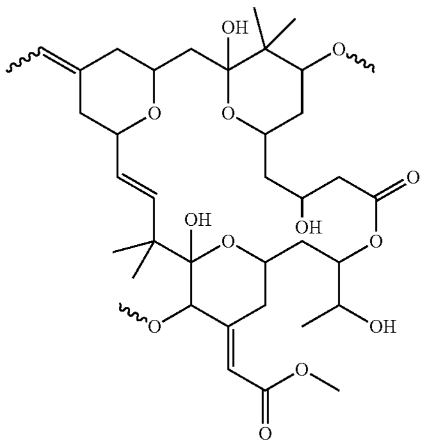

(IV)

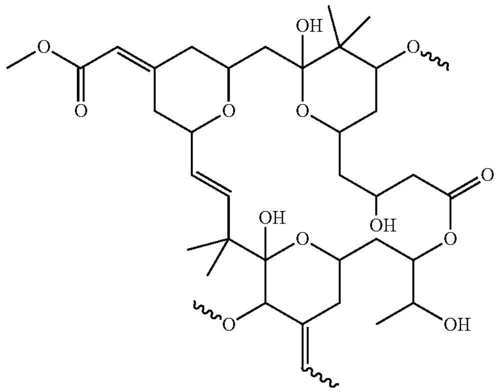

-continued (V)

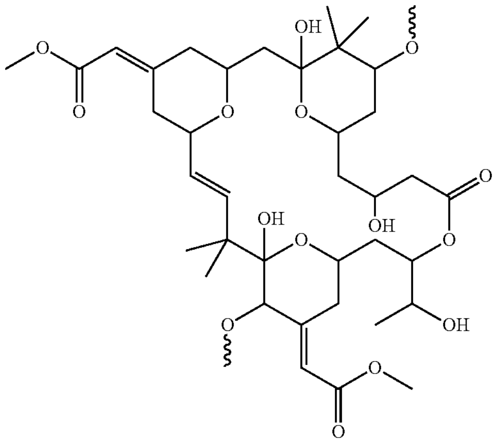

(VI)

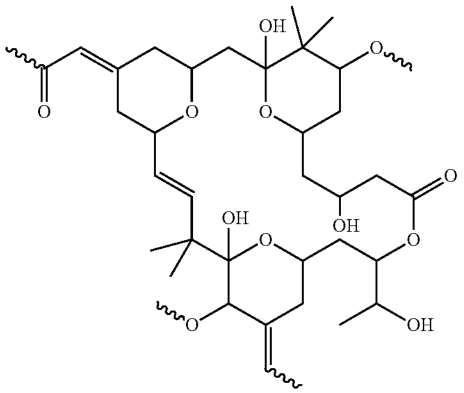

(VII)

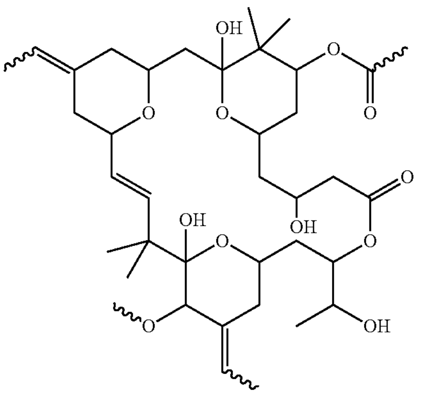

(VIII)

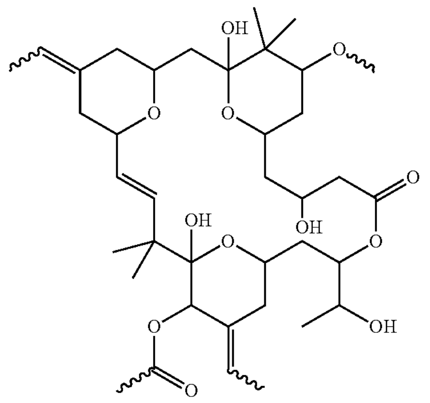

-continued (IX)

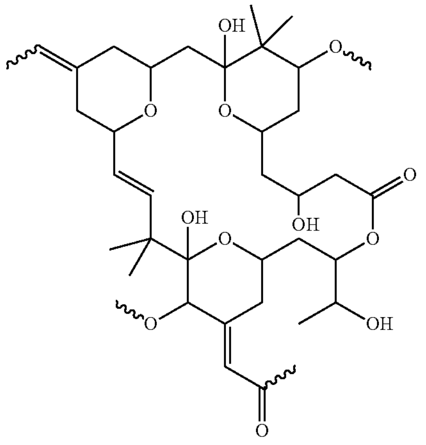

(X)

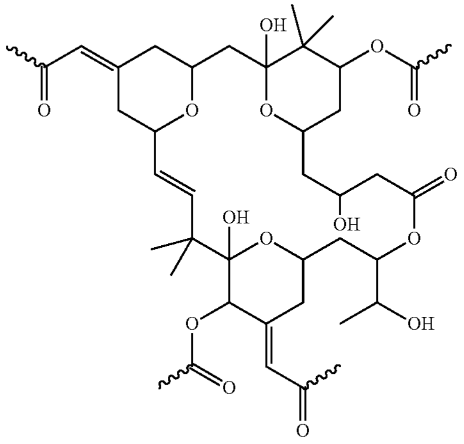

The term "derivative" as used herein refers to a bryostatin containing chemical modifications therein which may that retain or enhance its activity such as relative to byrostatin-1 in an in vitro or in vivo assay as disclosed herein. Any point of the molecule may be modified with one or more substituent, as permitted by the valency of the atoms at that point to form a bryostatin derivative. In some embodiments, one or more oxygen atom is modified with a substituent. In other embodiments, one or more carbon atom is modified with a substituent. In further embodiments, one or more carbon atom and one or more oxygen atom are modified with substituents, which may be the same or differ. The substituents may be chosen by one skilled in the art in an effort to retain or enhance the biological activity and potency of bryostatin-1. In some embodiments, the substituent is H, halo, $C_{1-6}$ haloalkyl, OH, $C_{1-6}$ alkyl, $C_{1-6}$ alkoxy, $C_{1-6}$ hydroxyalkyl, $C_{3-8}$ cycloalkyl, $C(O)C_{1-6}$ alkyl, $C(O)C_{1-6}$ alkoxy, $OC(O)C_{1-6}$ alkyl, $C_{2-8}$alkenyl, $C_{2-8}$alkynyl, aryl, heterocyclyl, or heteroaryl.

The term "alkyl" as used herein refers to straight- or branched-chain alkyl group having from 1 to about 12 carbon atoms ($C_{1-12}$), preferably 1 to 6 carbons atoms ($C_{1-6}$), in the chain. Examples of alkyl groups include methyl (Me) ethyl (Et), propyl (n-propyl or isopropyl), butyl (n-butyl, isobutyl, sec-butyl, or tert-butyl), pentyl (such as isopentyl or tert-pentyl), hexyl (such as isohexyl), and groups that in light of the ordinary skill in the art and the teachings provided herein would be considered equivalent to any one of the foregoing example.

The term "alkoxy" as used herein refers to a —O-alkyl group, wherein alkyl is defined above. In some preferred embodiments, the alkoxy group contains from 1 to 6 carbon atoms of a straight, branched, cyclic configuration and combinations thereof. Examples of alkoxy include, but are not limited to, methoxy, ethoxy, propoxy, isopropoxy, cyclopropyloxy and cyclohexyloxy.

The term "hydroxyalkyl" as used herein refers to straight- or branched-chain alkyl group, wherein the alkyl group is defined above and one or more hydrogen atom is replaced with an OH group. Examples of hydroxyalkyl groups include hydroxymethyl ($CH_2OH$) hydroxyethyl ($CH_2CH_2OH$ or $CH(OH)CH_3$), hydroxypropyl ($CH_2CH_2CH_2OH$, $CH_2CH(OH)CH_3$, $CH(OH)CH_2CH_3$, $C(OH)(CH_3)_2$, $CH(CH_3)(CH_2OH)$, $CH(CH_2OH)_2$), or hydroxybutyl ($CH_2CH_2CH_2CH_2OH$, $CH_2CH_2CH(OH)CH_3$, $CH_2CH(OH)CH_2CH_3$, $CH(OH)CH_2CH_2CH_3$, $CH(CH_3)CH_2CH_2OH$, $CH(CH_3)CH(OH)CH_3$, $CH(CH_2OH)CH_2CH_3$, $C(OH)(CH_3)CH_2CH_3$, $CH_2CH(CH_3)CH_2OH$, $CH_2CH(CH_2OH)CH_3$, $CH_2C(OH)(CH_3)CH_3$, $CH(OH)CH(CH_3)CH_3$, $C(CH_2OH)_3$, $C(CH_2OH)_2(CH_3)_2$, or $C(CH_2OH)(CH_3)_2$), among others, and groups that in light of the ordinary skill in the art and the teachings provided herein would be considered equivalent to any one of the foregoing example.

"Halo," or variations thereof, as used herein refers to fluoro, chloro, bromo or iodo.

The term "haloalkyl" as used herein include an alkyl as described wherein one or more hydrogen atom is replaced with halo. For example, the term "fluoroalkyl" includes a haloalkyl group in which the halo is fluorine. Preferred haloalkyl groups include, without limitation, $CF_3$.

The term "cycloalkyl" as used herein refers to a monocyclic or polycyclic radical that contains carbon and hydrogen, and is saturated or partially unsaturated. In some embodiments, cycloalkyl groups include groups having from 3 to about 12 ring atoms ($C_{3-12}$cycloalkyl), preferably $C_{3-8}$ cycloalkyl. Thus, a cycloalkyl having 3 to 12 carbon atoms includes a cycloalkyl group having 3 carbon atoms, 4 carbon atoms, 5 carbon atoms, etc., up to and including 12 carbon atoms. Illustrative examples of cycloalkyl groups include, but are not limited to cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents described herein.

The term "heterocyclyl" refers to a 3 to 10 membered, 4 to 8 membered, or 6 to 8 membered monocyclic or bicyclic, saturated ring structure containing at least one heteroatom, i.e., O, N, or S. The heterocyclyl group is attached at any heteroatom or carbon atom of the ring such that the result is a stable structure. Examples of heterocyclyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

The term "alkenyl" as used herein refers to a hydrocarbon group having at least two carbon atoms and at least one carbon-carbon double bond at any position in the group. In some embodiments, alkenyl includes $C_{2-6}$ alkenyl, $C_{2-5}$ alkenyl, or $C_{2-4}$ alkenyl. In some aspects, the alkenyl is $C_2$alkenyl, $C_3$alkenyl, $C_4$alkenyl, $C_5$alkenyl, or $C_6$alkenyl.

The term "alkynyl" as used herein refers to a hydrocarbon group having at least two carbon atoms and at least one carbon-carbon triple bond at any position in the group. In some embodiments, alkynyl includes $C_{2-6}$ alkynyl, $C_{2-5}$ alkynyl, or $C_{2-4}$ alkynyl. In some aspects, the alkynyl is $C_2$alkynyl, $C_3$alkynyl, $C_4$alkynyl, $C_5$alkynyl, or $C_6$alkynyl.

The term "aryl" as used herein refers to an aromatic radical with six to ten ring atoms ($C_{6-10}$) which has at least one ring having a conjugated pi electron system which is carbocyclic. The term includes monocyclic or fused-ring polycyclic (i.e., rings which share adjacent pairs of ring atoms) groups. In some embodiments, an aryl includes phenyl, fluorenyl, and naphthyl.

The term "heteroaryl" as used herein refers to a 5- to 18-membered aromatic radical ($C_{5-13}$heteroaryl) that includes one or more ring heteroatoms, i.e., N, O, or S, and which is a monocyclic, bicyclic, tricyclic or tetracyclic ring system. For example, an N-containing "heteroaryl" group refers to an aromatic group in which at least one of the skeletal atoms of the ring is a nitrogen atom. The polycyclic heteroaryl group may be fused or non-fused. The heteroatom in the heteroaryl radical is optionally oxidized and one or more N-atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10α-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl).

The bryostatin or bryostatin-1 described herein may contain one or more asymmetric centers, i.e., chiral centers. In some embodiments, the bryostatin or bryostatin-1 contains 1 to 11 or up to 14 chiral centers, i.e., 1, 2, 3, 4, 5, 6, 7, 8, 9, 10, 11, 12, 13, or 14 chiral centers. Preferably, the bryostatin or bryostatin-1 contains 6 to 12 chiral centers. More preferably, the bryostatin or bryostatin-1 contains 8 to 10 chiral centers. Thus, the bryostatin can thus give rise to isomeric forms that can be defined. The term "isomers" or "isomeric form" as used herein refers to bryostatin compounds or bryostatin-1 having the same molecular formula and include stereoisomers, enantiomers, diastereomers, and racemic mixtures thereof. The present chemical entities, pharmaceutical compositions and methods are meant to include all such possible isomers, including racemic mixtures, optically pure forms and intermediate mixtures.

In some embodiments, the bryostatin is bryostatin-1 of the structure:

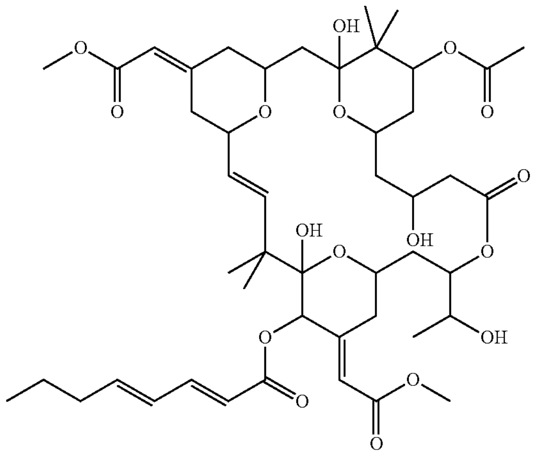

(bryostatin-1)

In other embodiments, the bryostatin is bryostatin-1 of the structure:

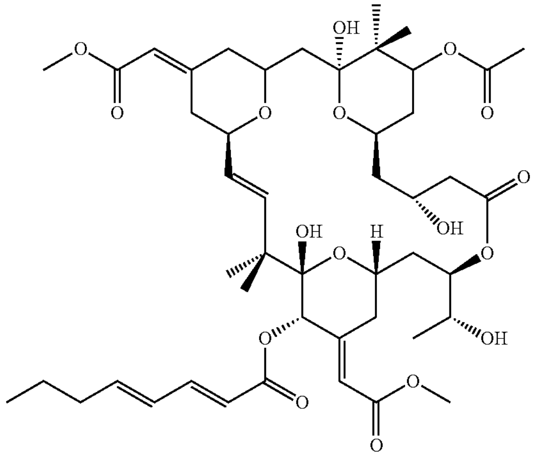

(bryostatin-1)

In other embodiments, the bryostatin derivative is any of:

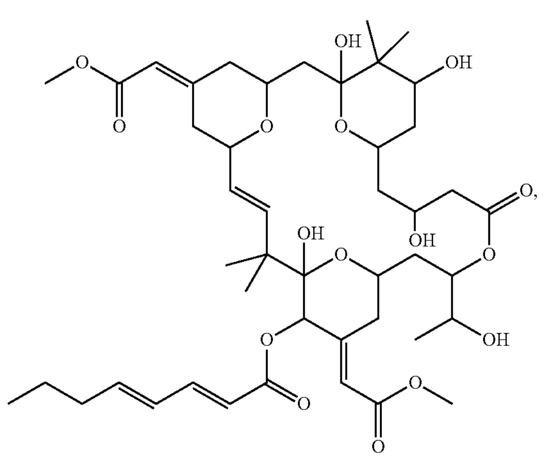

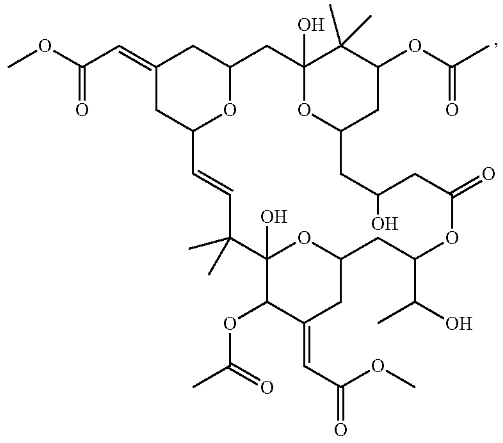

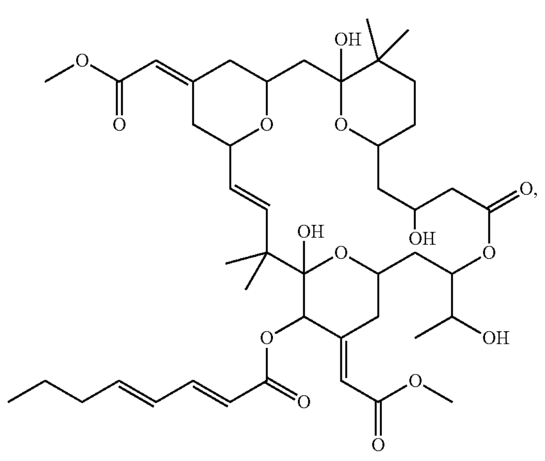

-continued
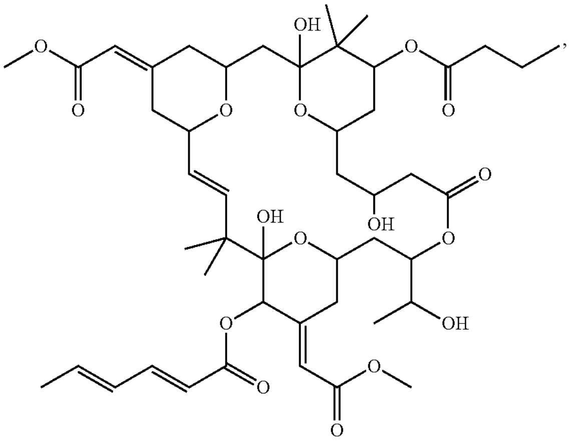
,
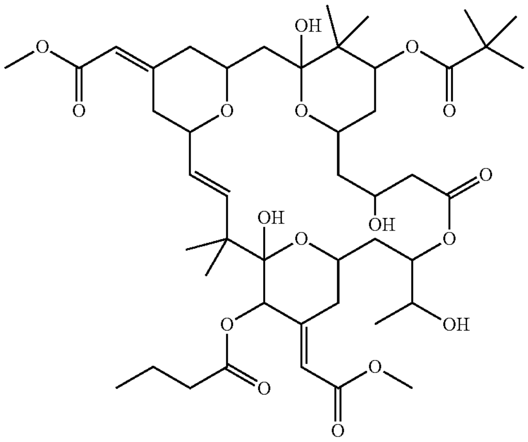
,
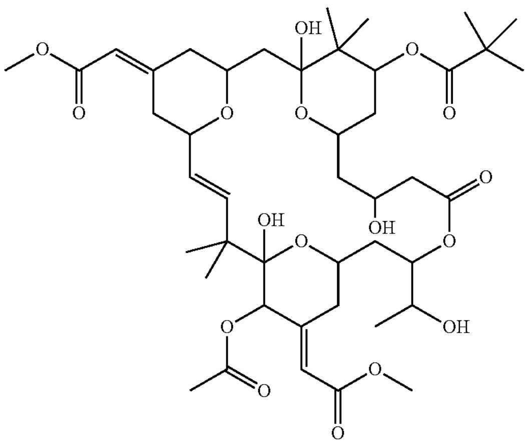
,
-continued
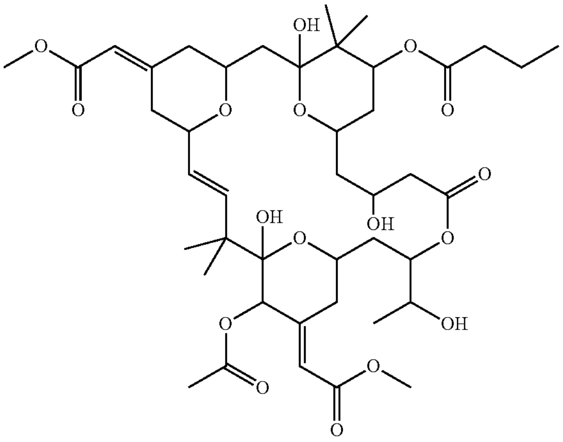
,
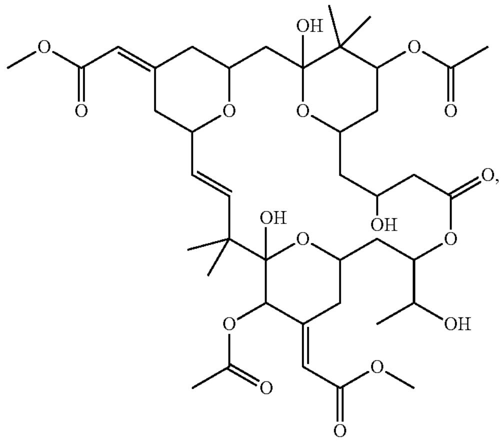
,
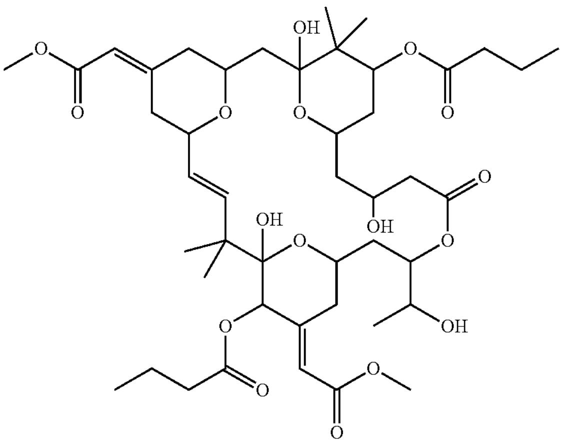
, -continued

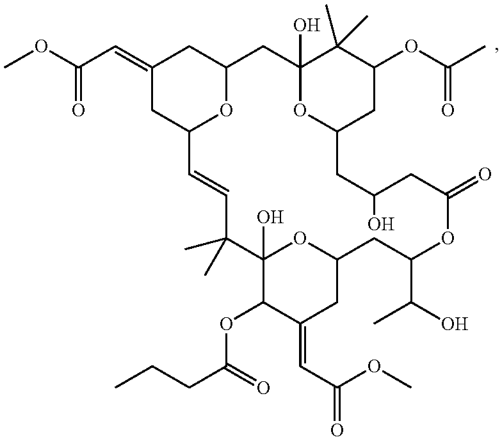
,

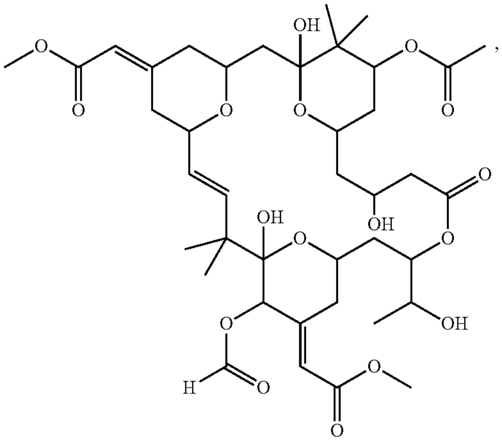
,

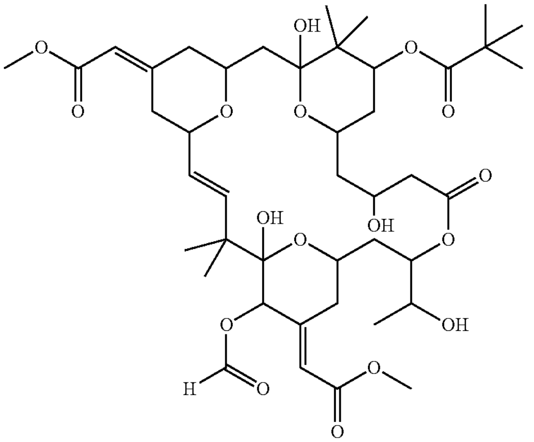
,

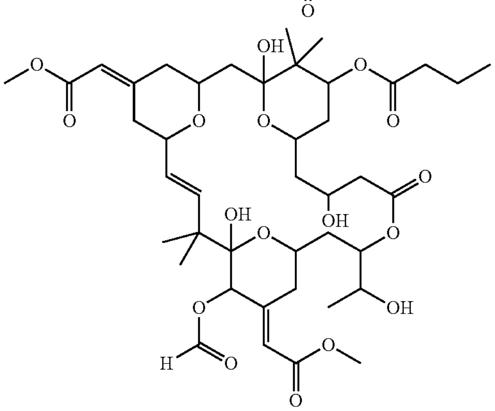
, or

-continued

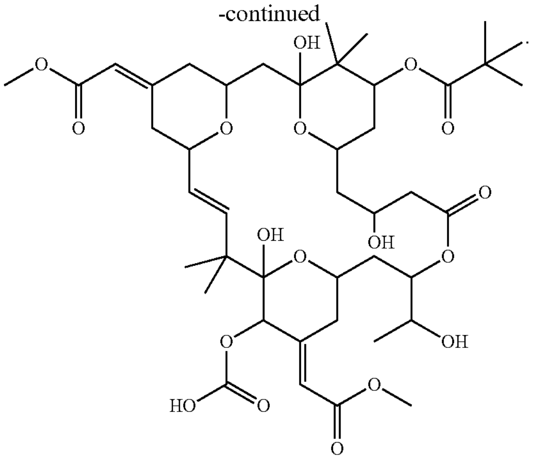

In further embodiments, the bryostatin may be selected from one of the bryostatin analogs described in Marsden, "Characterization of designed, synthetically accessible bryostatin analog HIV latency reversing agents," Virology, July 2018, 520:83-93; Marsden, "In vivo activation of latent HIV with a synthetic bryostatin analog effects both latent cell "kick" and "kill" in strategy for virus eradication," PLoS Pathog., September 2017, 13(9):e1006575; Albert, "Combinations of isoform-targeted histone deacetylase inhibitors and bryostatin analogues display remarkable potency to activate latent HIV without global T-cell activation," Sci. Rep., August 2017, 7(1):7456; Abdelnabi, "Comparative analysis of the anti-chikungunya virus activity of novel bryostatin analogs confirms the existence of a PKC-independent mechanism," Biochem. Pharmacol., November 2016, 120:15-21; Wender, "Improved protein kinase C affinity through final step diversification of a simplified salicylate-derived bryostatin analog scaffold," Org. Lett., October 2014, 16(19):5140-3; Wender, "Computer-guided design, synthesis, and protein kinase C affinity of a new salicylate-based class of bryostatin analogs," Org. Lett., Oct. 3, 2014, 16(19):5136-9; DeChristopher, "Picolog, a synthetically-available bryostatin analog, inhibits growth of MYC-induced lymphoma in vivo," Oncotarget, January 2012, 3(1): 58-66; Wender, "Design, synthesis, and evaluation of potent bryostatin analogs that modulate PKC translocation selectivity," Proc. Natl. Acad. Sci. USA, April 2011, 108(17): 6721-6; Wender, "The design, synthesis, and evaluation of $C_7$ diversified bryostatin analogs reveals a hot spot for PKC affinity," Org. Lett., August 2008, 10(15):3331-4; Wender, "Total synthesis and initial biological evaluation of new B-ring-modified bryostatin analogs," Org. Lett., November 2006, 8(23):5299-3021; Wender, "Synthesis and PKC binding of a new class of a-ring diversifiable bryostatin analogues utilizing a double asymmetric hydrogenation and cross-coupling strategy," Org. Lett., September 2006, 8(20): 4581-4; Wender, "Design, synthesis, and biological evaluation of a potent, PKC selective, B-ring analog of bryostatin," Org Lett, April 2006, 8(9):1893-6; Wender, "Function oriented synthesis: the design, synthesis, PKC binding and translocation activity of a new bryostatin analog," Curr. Drug Discov. Technol., January 2004, 1(1):1-11; Wender, "Role of the A-ring of bryostatin analogues in PKC binding: synthesis and initial biological evaluation of new A-ring-modified bryologs," Org Lett., May 2005, 7(10):1995-8; Wender, "Identification of a tunable site in bryostatin analogs: $C_{20}$ Bryologs through late stage diversification," Org.

Lett., March 2005, 7(6):1177-80; Baryza, "Simplified analogs of bryostatin with anticancer activity display greater potency for translocation of PKCδ-GFP," Chem. Biol., September 2004, 11(9):1261-7; Wender, "The practical synthesis of a novel and highly potent analogue of bryostatin," J. Am. Chem. Soc., November 2002, 124(46):13648-9; Wender, "The rational design of potential chemotherapeutic agents: synthesis of bryostatin analogues," Med. Res. Rev., September 1999, 19(5):388-4071 and Wender, "The design, computer modeling, solution structure, and biological evaluation of synthetic analogs of bryostatin 1," Proc. Natl. Acad. Sci USA, June 1998, 95(12):6624-9, all of which are hereby incorporated by reference. Other substitutions to one or more positions on bryo-1 may be used.

As discussed above, the term "bryostatin" also includes salts, such as pharmaceutically acceptable salts, thereof. A pharmaceutically acceptable salt includes salts with a pharmaceutically acceptable acid or base, e.g., inorganic acids such as hydrochloric acid, sulfuric acid, phosphoric acid, diphosphoric acid, hydrobromic acid, hydroiodic acid and nitric acid and organic acids such as citric acid, fumaric acid, maleic acid, malic acid, mandelic acid, ascorbic acid, oxalic acid, succinic acid, tartaric acid, benzoic acid, acetic acid, methanesulphonic acid, ethanesulphonic acid, benzenesulphonic acid, cyclohexylsulfamic acid or p-toluenesulphonic acid. Pharmaceutically acceptable bases include alkali metals, e.g., sodium or potassium, alkali earth metals, e.g., calcium or magnesium, hydroxides, and organic bases, e.g., alkyl amines, arylalkyl amines and heterocyclic amines.

The term "alkyl amine" as used herein refers to an alkyl group as previously described, wherein a H-atom is replaced with a $NH_2$ group or a carbon atom or an internal $CH_2$ is replaced with a NH moiety.

The term "arylalkyl amine" as used herein refers to the —NH(alkyl)(aryl) group, wherein the alkyl and aryl groups are previously described.

The term "heterocyclic amine" as used herein refers to a N-atom containing heterocyclyl previously described, wherein the amine is capable of conjugating to another moiety.

"Pharmaceutically acceptable" refers to properties and/or substances that are acceptable to the patient from a pharmacological/toxicological vantage, and to the manufacturing pharmaceutical chemist from a physical/chemical vantage regarding composition, formulation, stability, patient acceptance, and bioavailability.

The term bryostatin further includes prodrugs thereof. The term "prodrug" as used herein refers to a modified form of a bryostatin which modified form may be less therapeutically active. The modification made to the bryostatin permits in vivo conversion to the active bryostatin form. Prodrugs are known in the art and include esters, ethers, carbamates, peptides, and the like. See, e.g., the prodrugs described in Testa, "Prodrugs Revisited: The "Ad Hoc" Approach as a Complement to Ligand Design", Medicinal Research Reviews, 16(3):233-241, ed., John Wiley & Sons (1996), which is incorporated by reference herein.

The disclosure also provides methods for treating patients having symptoms of multiple sclerosis, comprising administering a therapeutically effective amount of a bryostatin to the patient. In doing so, the inventors found that the bryostatin provides an anti-inflammatory effect, immunosuppressive effect, a neuromodulatory effect, or a combination thereof. In some embodiments, the bryostatin was found to repair damage to neurons, axons, or myelin in the patient, which is an unprecedented action of agents used for treating MS. Also unprecedented is the ability of the bryostatin to increase remyelination of neurons.

In some embodiments, the bryostatin reduces one or more symptoms associated with multiple sclerosis (MS) or other indication as disclosed herein such as a neuroinflammatory disorder, Amyotrophic Lateral Sclerosis; or a demyelinating disease or disorder or a hypomyelinating condition. The term "symptom" as used herein refers to a physical, mental, or cognitive feature that is indicative of the patient having multiple sclerosis. In some embodiments, the patient has one or more symptom of MS and may be aware of the symptom. The symptoms may be initial, i.e., a primary symptom, or may appear after the original onset of the disease, i.e., a secondary symptom that arises as a result of the primary symptom or a tertiary symptom which is a social, vocational and/or psychological complication of the primary and/or secondary symptom. In some embodiments, the symptom is a physical or mental symptom including, without limitation, blurred vision, double vision, red-green color distortion, difficulty walking, paresthesia (abnormal sensation, pain, numbness, prickling, or "pins and needles"), pain and/or loss of vision due to optic neuritis, muscle weakness, difficulty with coordination, spasticity, fatigue, loss of sensation, speech impediments, tremor, dizziness, hearing loss, bowel disturbances, bladder disturbances, depression, anxiety, mania, or changes in sexual function, or a combination thereof. In other embodiments, the symptom is a cognitive symptom including, without limitation, concentration, attention, memory, or poor judgement, or a combination thereof. In yet further embodiments, the symptom is one or more of limb numbness, limb weakness, vision loss, a visual dysfunction such as double vision, pain, tingling, electric-shock sensations, tremor, coordination loss, balance loss, gait impairment, dizziness, slurred speech, fatigue, cognitive impairment, depression, anxiety, or mania. In further embodiments, the symptom is a neurological symptom.

The disclosure also provides methods for preventing the onset of multiple sclerosis symptoms in patient having multiple sclerosis or those patients predisposed to multiple sclerosis, comprising administering a therapeutically effective amount of a bryostatin to the patient.

As discussed, treatment methods include identifying a patient that is suffering from a disease or disorder as disclosed herein and then administering an effective amount of a bryostatin compound to the identified patient.

Identifying a patient as suffering from a disease or disorder as disclosed herein, including multiple sclerosis, neuroinflammatory disorder or disease, Amyotrophic Lateral Sclerosis, or a demyelinating disease or disorder or a hypomyelinating condition can be performed in accordance with reported procedures. See The Merck Manual (including 16th ed., Vol. 1 sections entitled "Demyelinating Diseases" and "Multiple Sclerosis", as well as subsequent editions). See also US 2016/0015659 and US2019/0314338.

The methods described herein also include administering an adjunctive therapy to the patient. As used herein, "adjunctive therapy" as used herein refers to another therapy that is in addition to administration of a bryostatin. In some embodiments, the adjunctive therapy is another agent, physical therapy, plasma exchange, or a combination thereof.

In some aspects, the methods include administering another agent with the bryostatin. In some embodiments, the another agent is effective for treating multiple sclerosis or one or more symptoms of multiple sclerosis. The another agent may be administered concurrently with the bryostatin, subsequent to the bryostatin, or before the bryostatin. In some embodiments, the bryostatin is administered concurrently with the another agent. In other embodiments, the bryostatin is administered prior to the another agent. In further embodiments, the bryostatin is administered after the another agent.

In other embodiments, the another agent is an anti-inflammatory agent, muscle relaxant, cytokines, an antibody, an immunosuppressant, an immunomodulator, a remyelinating agent, or dimethyl fumarate. In further embodiments, the another agent is an anti-inflammatory agent such as a corticosteroid. In yet other embodiments, the another agent is prednisone or methylprednisolone. In still further embodiments, the another agent is a muscle relaxant, such as baclofen or tizanidine. In other embodiments, the another agent is an cytokines such as (3-interferon and IL-4. In further embodiments, the another agent is an antibody, such as ocrelizumab, natalizumab, or alemtuzumab. In yet other embodiments, the another agent is an immunosuppressant such as mitoxantrone. In still further embodiments, the another agent is an immunomodulatory agent, such as glatiramer acetate, teriflunomide, or fingolimod. In other embodiments, the another agent is dimethyl fumarate.

The bryostatin may also be administered in conjunction with physical therapy. The physical therapy is desirably performed as determined by the attending physician and/or physical therapist.

The bryostatin may be used alone or in combination with one or more additional ingredients, i.e., active agents, such as the another agents previously described, or inactive agents, to formulate pharmaceutical compositions of the disclosure. In some embodiments, the disclosure provides pharmaceutical compositions comprising (a) an effective amount of at least one bryostatin in accordance with the disclosure; and (b) a pharmaceutically acceptable excipient. In other embodiments, the disclosure provides pharmaceutical compositions comprising at least one bryostatin and an agent effective for treating multiple sclerosis as provided above.

A suitable or effective amount of bryostatin administered is determined by the attending physician depending on the patient, severity and progression of the disease, and aggressiveness of the treatment. In some embodiments, the amount of the bryostatin administered to the patient is about 1 ng/kg to 100 mg/kg, based on the weight of the patient. Alternatively, in some embodiments, the amount of bryostatin is about 1 to about 200 $\mu g/m^2$ body surface area, based on the surface area of an average human. Preferably, the amount of bryostatin is about 10 to 120 $\mu g/m^2$ body surface area. As used herein, the average human has a surface area of about 1.5 to about 2.5 $m^2$, preferably about 1.5 to about 2 $m^2$.

"Pharmaceutically acceptable excipient" as used herein refers to a diluent, adjuvant, vehicle or carrier with which a bryostatin described herein is administered. A pharmaceutically acceptable excipient refers to a substance that is non-toxic, biologically tolerable, and otherwise biologically suitable for administration to a subject, such as an inert substance. The excipient may be added to the composition or otherwise used as a vehicle, carrier, or diluent to facilitate administration of an agent. Preferably, the excipient is compatible with the bryostatin. Examples of excipients include inert diluents, disintegrating agents, binding agents, lubricating agents, sweetening agents, flavoring agents, coloring agents and preservative agents. Specific examples of excipients include, without limitation, calcium carbonate, calcium phosphate, various sugars and types of starch, cellulose derivatives, gelatin, vegetable oils, and polyethylene glycols.

The bryostatins alone or pharmaceutical formulations containing same may be administered by any route that would be acceptable for administration of bryostatin-1. In some embodiments, the pharmaceutical formulations the administration is oral, intravenous, transdermal, parenteral, intrathecal, rectal, topical, ocular, by inhalation, or a combination thereof. In further embodiments, administration is oral. In other embodiments, administration is intravenous. In yet further embodiments, administration is transdermal. In still other embodiments, administration is parenteral. In further embodiments, administration is intrathecal. In other embodiments, administration is rectal. In still further embodiments, administration is topical. In yet other embodiments, administration is ocular. In further embodiments, administration is by inhalation.

The bryostatin of this disclosure may also be administered by non-oral routes. For example, the compositions may be formulated for rectal administration as a suppository. For parenteral use, including intravenous, intramuscular, intraperitoneal, intrathecal, or subcutaneous routes, the bryostatin may be provided in sterile aqueous solutions or suspensions, buffered to an appropriate pH and isotonicity or in parenterally acceptable oil. Suitable aqueous vehicles include Ringer's solution and isotonic sodium chloride.

The pharmaceutical formulations may be formulated for administration in solid or liquid forms. In some embodiments, the pharmaceutical formulations are formulated in the form of a tablet, caplet, capsule, powder, softgel, suspension or liquid, or a combination thereof. In other embodiments, the pharmaceutical formulations are formulated in the form of a tablet. In further embodiments, the pharmaceutical formulations are formulated in the form of a caplet. In yet other embodiments, the pharmaceutical formulations are formulated in the form of a capsule. In still further embodiments, the pharmaceutical formulations are formulated in the form of a powder. In other embodiments, the pharmaceutical formulations are formulated in the form of a softgel. In further embodiments, the pharmaceutical formulations are formulated in the form of suspension. In yet other embodiments, the pharmaceutical formulations are formulated in the form of a liquid.

The disclosure also provides pharmaceutical kits comprising a bryostatin and instructions for using the bryostatin for treating multiple sclerosis. The pharmaceutical kit may optionally further include an agent that is effective for treating multiple sclerosis, such as those described The following Examples are provided to illustrate some of the concepts described within this disclosure. While each Example is considered to provide specific individual embodiments of formulations, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for.

EXAMPLES

Example 1: Materials and Methods

I. Reagents and Antibodies

Bryo-1 was purchased from Tocris (catalog #2383). $MOG_{35-55}$ peptide (amino acid sequence MEVGWYR-SPFSRVVHLYRNGK) was prepared by the Johns Hopkins Synthesis and Sequencing Core Facility, but may be purchased commercially. Incomplete Freund's adjuvant was purchased from Thermo Scientific (catalog #77145), and complete Freund's adjuvant was prepared by adding 8 mg/mL heat-killed *Mycobacterium tuberculosis* H37 Ra (Difco, catalog #231141). Pertussis toxin was purchased from List Biologicals (catalog #181). LPS from *Escherichia coli* 055:B5 was purchased from Sigma (catalog #L6529). Flow antibodies against CD4 (46-0042-82), CD40 (17-0401-82), CD44 (47-0441-82), FoxP3 (12-5773-82), and IL-17a (17-7177-81) were purchased from eBioscience. Antibodies against IFNγ (505806) and CD86 (105008) were purchased from Biolegend.

II. Mice

Wild-type C57BL/6J mice were purchased from the Jackson Laboratory. All mice were housed in a dedicated Johns Hopkins mouse facility. All protocols were approved by the Johns Hopkins Institutional Animal Care and Use Committee.

III. Induction and Scoring of EAE

Experimental autoimmune encephalomyelitis (EAE) is an experimental animal model that recapitulates some aspects of MS. In the active-induction model of mouse EAE, mice are immunized with a peptide derived from myelin oligodendrocyte glycoprotein ($MOG_{35-55}$), resulting in robust CNS inflammation causing demyelination, axonal injury, and motor weakness/paralysis.

Active EAE was induced in 8-12 wk-old female C57BL/6J mice that had been allowed to acclimatize to the animal facility for at least 1 wk. $MOG_{35-55}$ peptide dissolved in PBS at a concentration of 2 mg/mL was mixed 1:1 with complete Freund's adjuvant to make an emulsion. On day 0, mice were immunized by injecting 50 μL of the emulsion s.c. into each of two sites on the lateral abdomen. In addition, on day 0 and again on day 2, mice were injected intraperitoneally with 250 ng pertussis toxin. Mice were weighed and scored beginning on day 7 post-immunization. Scoring was performed in a blinded manner according to the following scale:

| Score | Summary |
|---|---|
| 0 | no clinical deficit |
| 0.5 | partial loss of tail tone |
| 1.0 | complete tail paralysis or both partial loss of tail tone plus awkward gait |
| 1.5 | complete tail paralysis and awkward gait |
| 2.0 | tail paralysis with hind limb weakness evidenced by foot dropping between bars of cage lid while walking |
| 2.5 | hind limb paralysis with little to no weight-bearing on hind limbs (dragging) but with some movement possible in legs |
| 3.0 | complete hind limb paralysis with no movement in lower limbs |
| 3.5 | hind limb paralysis with some weakness in forelimbs |
| 4.0 | complete tetraplegia but with some movement of head |
| 4.5 | moribund |
| 5.0 | dead |

IV. Preparation of Bryo-1 for Treatment of Cultured Cells

For treatment of cultured cells, bryo-1 was dissolved in 100% ethanol to a final concentration of 20 μM, which was subsequently used for treatment. Ethanol alone was used as vehicle control.

V. Preparation of Mouse Tissue for Flow Cytometry

Mice were killed with pentobarbital and perfused via cardiac puncture with ice-cold HBSS without cations. Brain, spinal cord (collected using hydrostatic pressure), spleen, and lymph node tissue were isolated after perfusion and were mechanically dissociated by passing through 100-μm cell strainers. For CNS tissue, after dissociation, infiltrating mononuclear cells were separated from myelin debris using a 37/70% percoll gradient. After dissociation, spleens were incubated in ACK lysis buffer to remove red blood cell contamination. Cells were counted using a MACSQuant flow cytometer (Miltenyi Biotec).

VI. Flow Cytometry and Intracellular Cytokine Staining

All staining procedures were performed in the dark at room temperature. For analysis of surface marker expression on bone marrow-derived DCs, cells were first stained with LIVE/DEAD aqua (Life Technologies, L-34966) for 30 min at room temperature in PBS. Fc receptors were blocked with anti-CD16/CD32 (Biolegend, 101320) for the final 10 min of staining. The cells were then washed and stained with specific conjugated antibodies for the specified surface markers in FACS buffer (PBS supplemented with 2% FBS and 1 mM EDTA) for 30 min.

For surface marker and intracellular cytokine staining of T cells, the cells were first restimulated with a cell stimulation mixture with protein transport inhibitors (eBioscience, catalog #00-4975-03) for 4 h in cRPMI at 37° C. They then underwent live/dead and surface marker staining as earlier. For intracellular cytokine staining, cells were permeabilized and fixed using either IC Fixation buffer for cytokine analysis (eBioscience, 00-8222-49) or FoxP3 fixation/permeabilization buffer for transcription factor analysis (eBioscience, 00-5521-00) after manufacturer recommended protocol and incubated with specific conjugated antibodies for the specified proteins in permeabilization buffer for 1 h.

Cells were analyzed by flow cytometry using a MACSQuant flow cytometer (Miltenyi Biotec). Flow data analysis was performed in FlowJo (FlowJo) or FlowLogic (Inivai).

VII. Preparation and Treatment of Murine BMDCs

BMDCs were generated as described in Lutz, "An advanced culture method for generating large quantities of highly pure dendritic cells from mouse bone marrow," 1999, J. Immunol. Methods 223:77-92, with minor modifications. Briefly, femurs were removed from 6-10-wk-old female C57BL/6J mice, cut on both ends, and marrow flushed with PBS. Bone marrow cells were then pelleted by centrifugation (500×g for 8 min), resuspended in red blood cell lysis buffer (Sigma) for 1 min, and quenched with excess PBS. After another centrifugation, cells were resuspended in complete RPMI (cRPMI) media consisting of RPMI-1640 with GlutaMAX™ supplement (Thermo Fisher Scientific) supplemented with 10% FBS, penicillin-streptomycin (Gibco), and 50 μM 2-mercaptoethanol (Sigma). On day 0, ~2×106 cells were then seeded per 100-mm plate in 10 mL media containing 20 ng/mL rmGM-CSF (Peprotech). On day 3, an additional 10 mL fresh cRPMI media containing 20 ng/mL rmGM-CSF was added to each plate. On day 6, half the culture supernatant from each plate was removed and centrifuged, and the pelleted cells resuspended in 10 mL fresh cRPMI with 20 ng/mL rmGM-CSF and added back to the plates. On day 8, all nonadherent cells (representing the BMDC fraction) were collected, pelleted by centrifugation, resuspended in fresh cRPMI media with 20 ng/mL rmGM-CSF, and plated into 24-well dishes. These BMDCs were then treated overnight with or without LPS 100 ng/mL plus the indicated doses of bryo-1. The following day (day 9), these cells were then assayed by flow cytometry or cytokine ELISA.

VIII. Statistical Analyses

For comparison of clinical scores in EAE experiments, Mann-Whitney U test was performed. For all other statistical analyses, two-tailed Student's t tests were used. All error bars depict SEM.

IX. Western Blotting

Cells were lysed by sonication in RIPA buffer supplemented with protease inhibitors, and protein concentration was measured by Bradford assay. Lysates were mixed with SDS sample buffer, boiled, and resolved by SDS/PAGE. Bands were transferred to PVDF Immobilon P membranes (Millipore) using a wet transfer, blocked in TBS-T containing 5% milk, and probed overnight at 4° C. with mouse monoclonal antibody against arginase-1 (Santa Cruz Biotechnology, catalog #sc-271430, 1:500). HRP-conjugated anti-mouse secondary antibody was from Jackson ImmunoResearch. Western blots were visualized using the SuperSignal West ECL system (Thermo Scientific), followed by film exposure. Blots were then stripped using Restore Western blot stripping buffer (Thermo Scientific, catalog #21059), blocked again as earlier, and probed overnight at 4° C. with HRP-conjugated anti-actin antibody before visualization as earlier. Quantitation was performed using ImageJ software.

X. ELISA

After overnight treatment of BMDCs or mPMs with LPS 100 ng/mL±bryo-1, culture supernatants were collected and cytokine production was assayed using ELISA kits for IL-12 p70 (catalog #88-7121-22), IL-6 (catalog #88-7064-22), and IL-10 (catalog #88-7105-22) purchased from eBioscience, according to manufacturer's instructions. Plates were read at 450 nm on a tabletop plate reader.

XI. Preparation of Naive $CD4^+$ T Cells

Spleens were harvested from 6-10-wk-old female C57BL/6J mice, and single-cell suspensions were generated in FACS buffer by disrupting spleens with the plunger of a syringe over a 70-μm nylon cell strainer (BD Falcon), pelleting cells by centrifugation (500×g for 8 min), and resuspending in fresh FACS buffer. Naive $CD4^+$ cells were then isolated by negative selection using an isolation kit from STEMCELL Technologies (catalog #19765).

XII. Stimulation of Naive $CD4^+$ T Cells with α-CD3/CD28 Antibodies

Tissue culture plates were coated with α-CD3 antibody (BD Biosciences) by incubating them with 0.25-1.0 m/mL of antibody diluted in sterile PBS overnight at 4° C. or for 2-4 h at 37° C. The antibody solution was then removed, plates were washed once with sterile PBS, and naive $CD4^+$ T cells were seeded along with 0.25-1.0 m/mL α-CD28 antibody (BD Biosciences) in the presence or absence of the indicated doses of bryo-1. The cells were cultured for 3 d and then analyzed by flow cytometry.

Example 2: Treatment of Mice with Bryo-1

Bryo-1 was prepared by initially dissolving in 100% ethanol and then further diluting to 20% ethanol and 1% DMSO in PBS. The final concentration of bryo-1 was 10 m/mL Mice were treated by i.p. injection of 30 m/kg bryo-1 or an equal volume of vehicle control (20% ethanol and 1% DMSO in PBS) 3 d per week (Monday, Wednesday, Friday).

In one set of experiments, treatment began on the same day as immunization with $MOG_{35-55}$ (day 0).

In a second set of experiments, mice were randomized and treatment was begun when the mice reached a clinical score of 1.0 (corresponding to tail paralysis). In this paradigm, mice received their first treatment on the day they reached a score of 1.0, and subsequently were returned to a 3 d/week schedule in sync with the other animals.

In a third set of experiments, mice were randomized and treatment was begun on day 28 post-immunization, more than 10 d after peak disease and once motor deficits had reached a stable plateau.

Example 3: Bryo-1 Prevents the Induction of EAE

EAE was elicited by immunizing 8-12-wk-old C57BL/6J mice with $MOG_{35-55}$. Neurologic symptoms of EAE were most evident 10-14 d after MOG immunization, peaking at about 16 d and then plateauing with slight diminution until 21 d. Mice were treated with bryo-1 (30 μg/kg) or vehicle by i.p. injection 3 d per week.

Figure 1A:
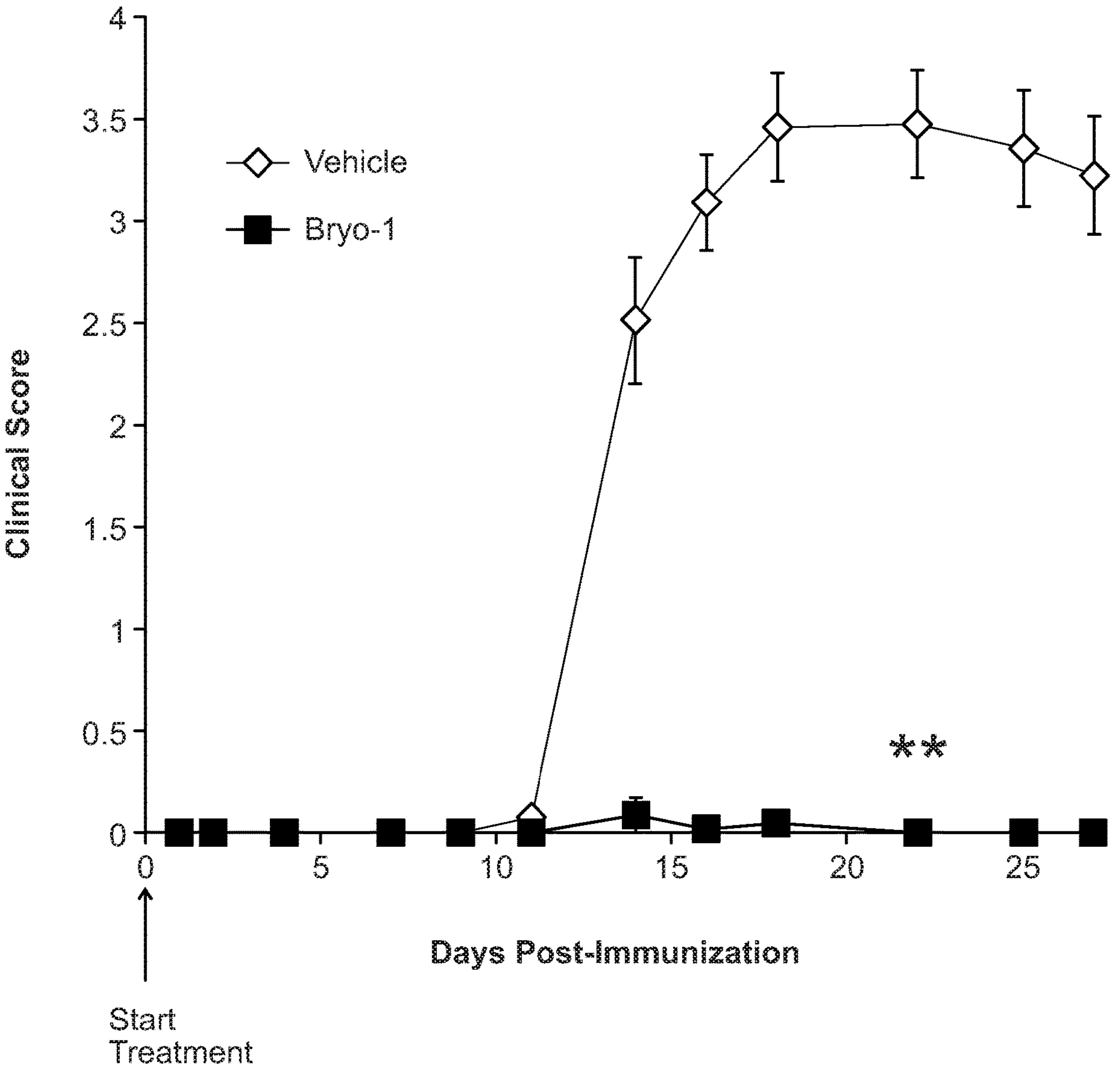
FIG. 1A is a line graph showing the clinical course of mice treated with bryo-1 (30 μg/kg) or vehicle alone by i.p. injection 3 d per week, beginning on the day of immunization (day 0) with myelin oligodendrocyte glycoprotein ($MOG_{35-55}$)(day 0); n=19 and 15 mice in vehicle and bryo-1 groups, respectively. Error bars represent SEM.
Figure 1B:
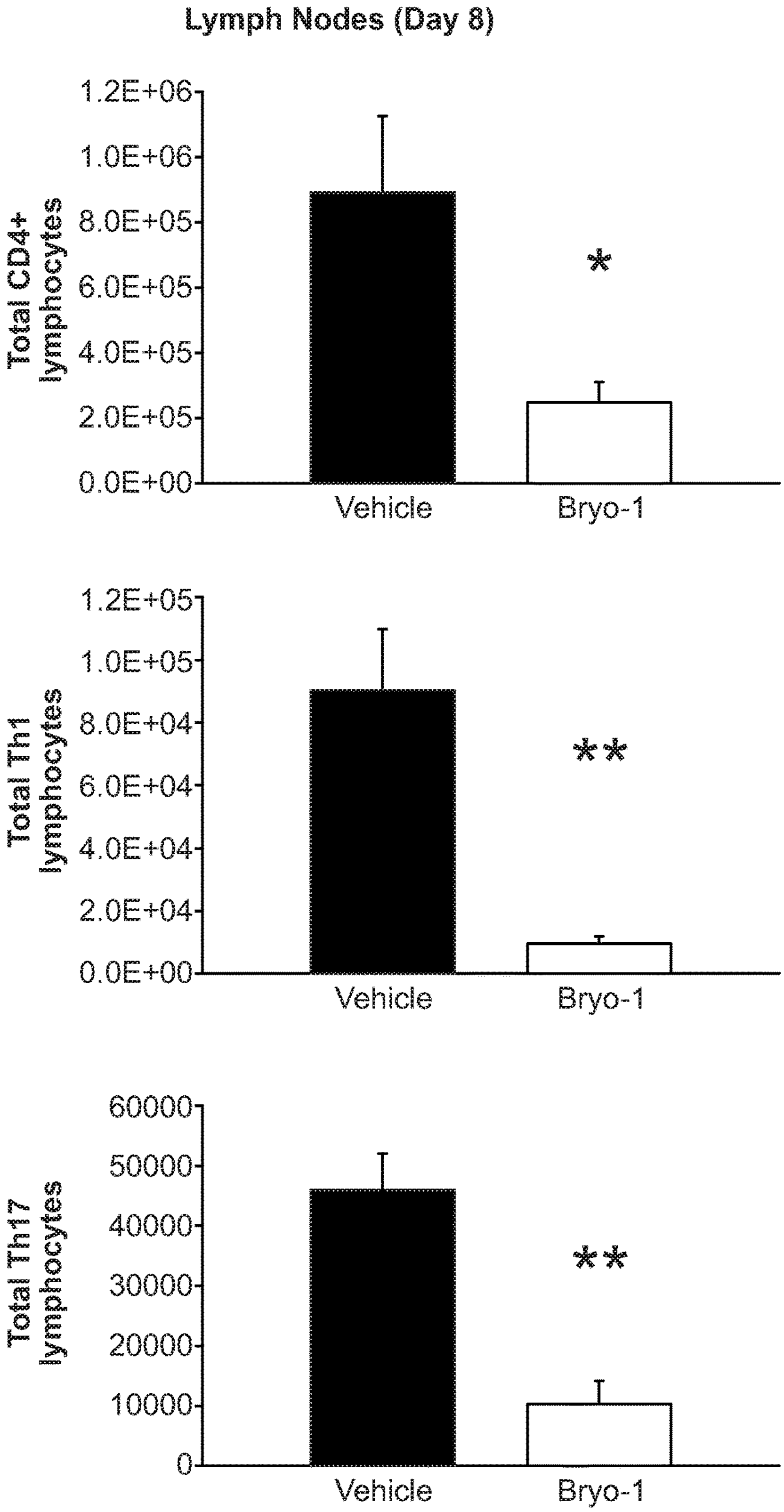
FIGS. 1B and 1C show the flow cytometry data from lymph nodes in EAE mice at day 8 post-immunization; n=5 mice per group.
Figure 1C:
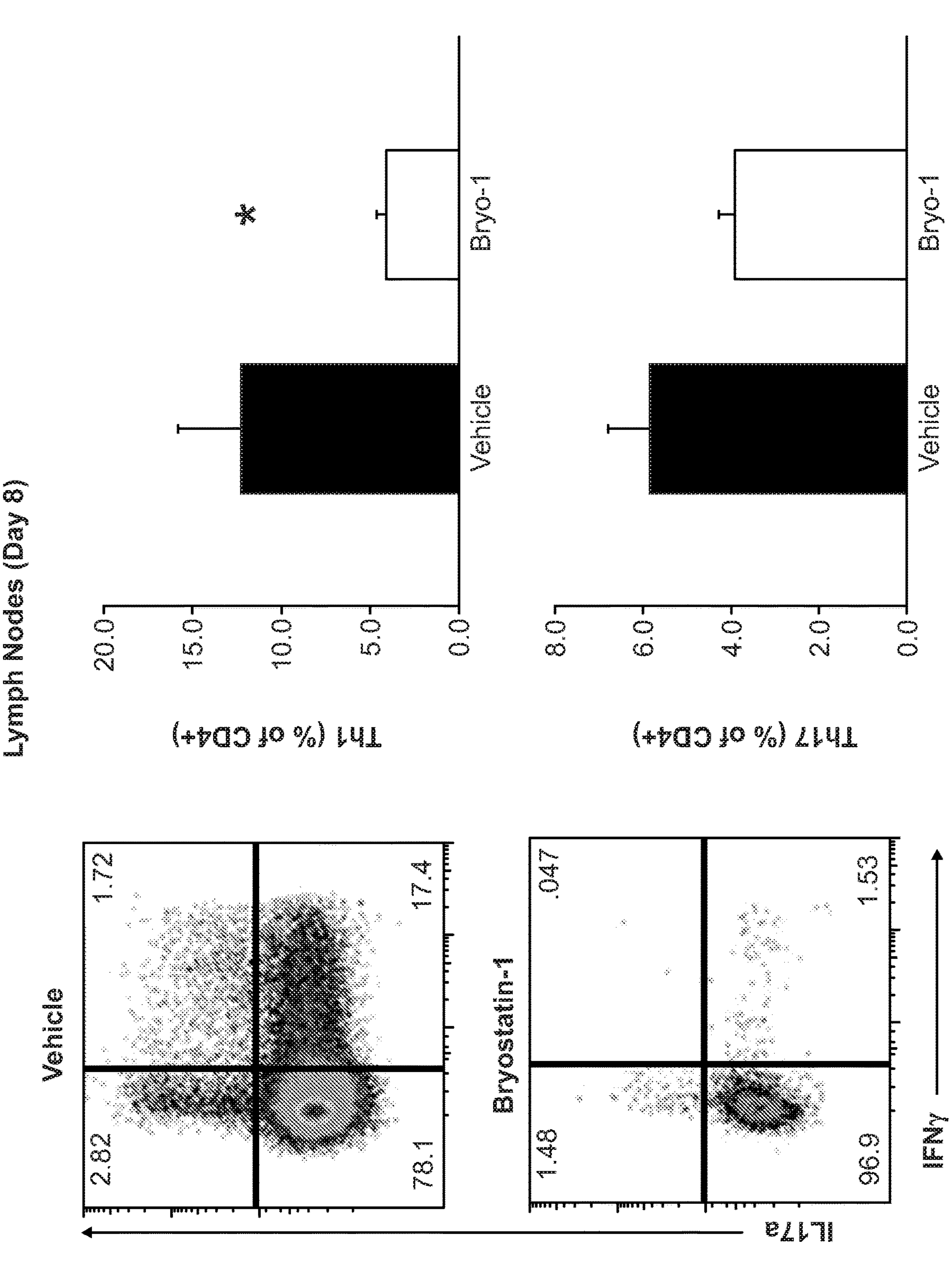
Figure 1D:
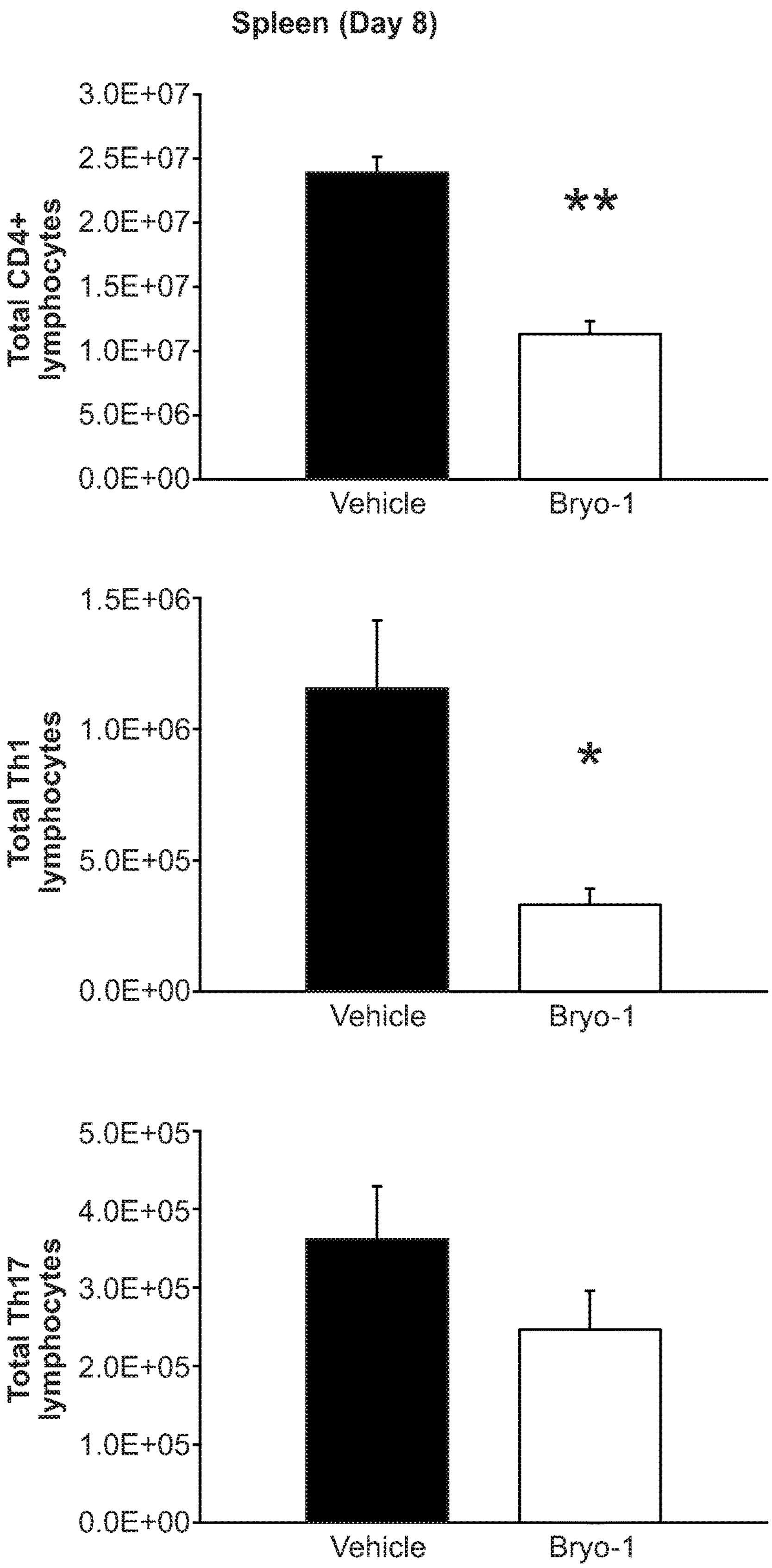
FIG. 1D are bar graphs showing the flow cytometry data from spleen in experimental autoimmune encephalomyelitis (EAE) mice on day 8, depicting total numbers of $CD4^+$, Th1, and Th17 lymphocytes; n=5 mice per group.

In initial experiments, treatment began on the day of $MOG_{35-55}$ immunization (day 0). In this prevention paradigm, bryo-1 treatment abolished the onset of EAE (FIG. 1A), suggesting that bryo-1 prevents the pathogenic peripheral immune response to $MOG_{35-55}$ immunization. Consistent with this hypothesis, flow cytometry from lymph nodes 8 d after immunization revealed significantly decreased numbers of total $CD4^+$ ($CD3^+$; $CD4^+$), Th1 ($CD4^+$; $IFN\gamma^+$), and Th17 ($CD4^+$; $IL17^+$) lymphocytes with bryo-1 treatment (FIG. 1B). Among $CD4^+$ lymphocytes, a significantly lower proportion of Th1 cells was observed with bryo-1 treatment, with insignificant decrease in the proportion of Th17 cells (FIG. 1C). Similarly, flow cytometry from spleen at day 8 revealed significantly decreased numbers of total $CD4^+$ and Th1 lymphocytes with bryo-1 treatment, with a trend toward decreased Th17 cells (FIG. 1D).

Figure 1E:
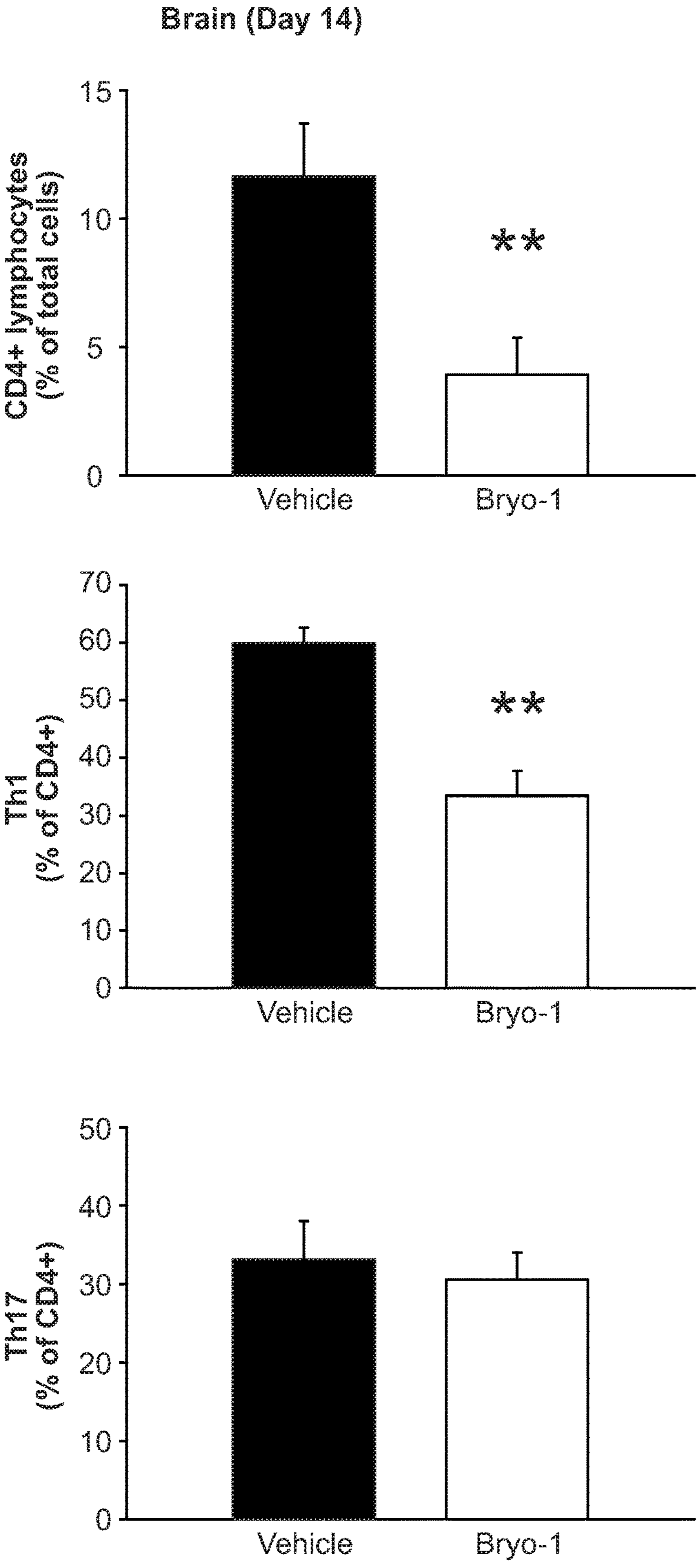
FIGS. 1E and 1F are bar graphs of the flow cytometry analysis of infiltrating $CD4^+$ lymphocytes in brain (E) and spinal cord (F) at peak EAE (day 14); n=9 mice per group. All error bars represent SEM. Statistical significance was determined by Mann-Whitney U test for EAE clinical scoring and by two-tailed Student's t test for flow cytometry data (*P<0.05; **P<0.01).
Figure 1F:
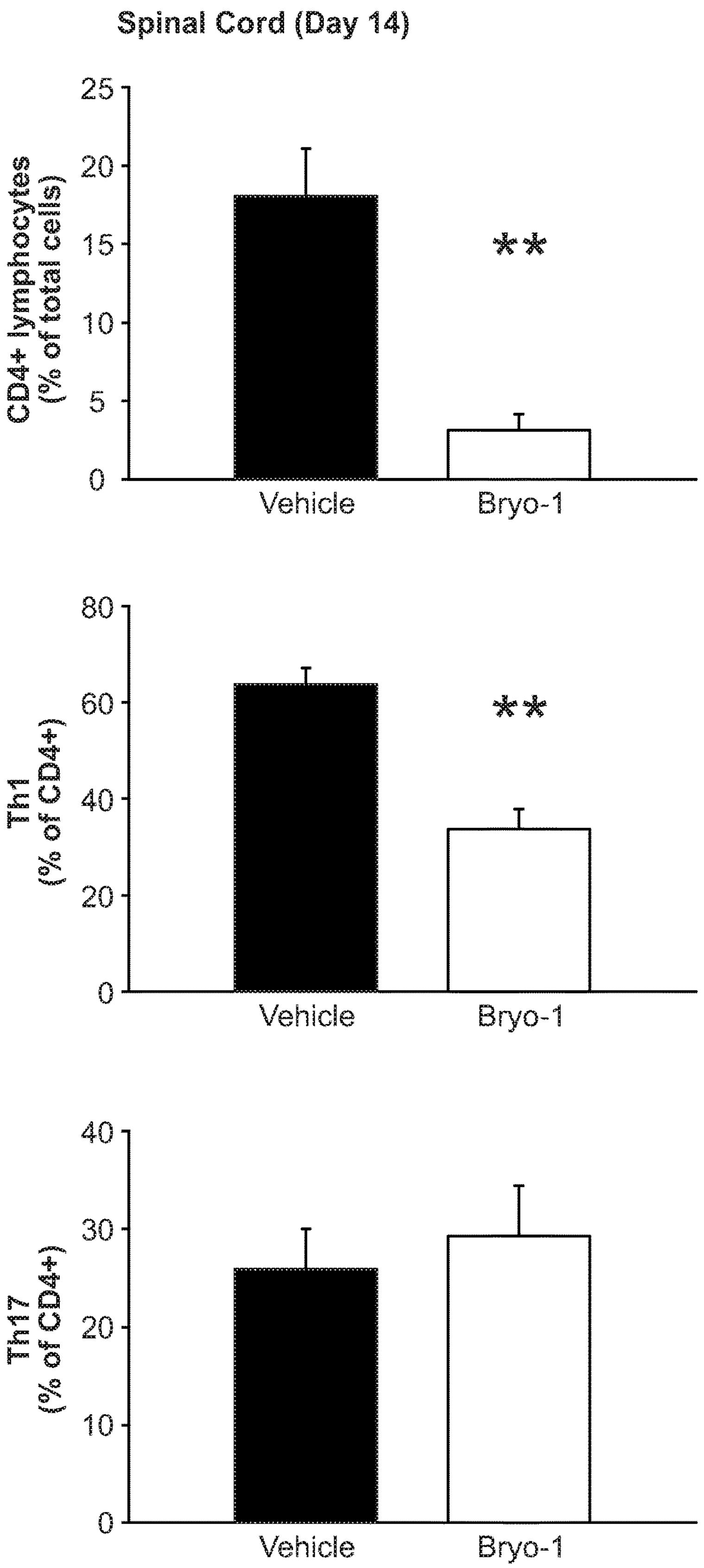

Consistent with the diminished peripheral immune response, prophylactic bryo-1 led to diminished infiltration of $CD4^+$ lymphocytes into the brain (FIG. 1E) and spinal cord (FIG. 1F) at peak disease (day 14), with a decreased proportion of $CD4^+$ lymphocytes producing IFNγ. The percentage of infiltrating $CD4^+$ lymphocytes expressing IL17 was unchanged with bryo-1 treatment.

This example demonstrates the striking finding of the marked beneficial effect of bryo-1 on EAE, whether administered concurrently with immunization, at the onset of neurologic signs, or as late as 28 d post-immunization, when the peak inflammatory phase has ended and neurologic disability has stabilized. This beneficial effect of bryo-1 occurs at a very low dose (30 m/kg) administered only 3 d per week and is associated with broadly decreased inflammation both in the CNS and in the periphery, as assessed by flow cytometry. Furthermore, direct and potent (as low as 10 nM) anti-inflammatory effects of bryo-1 on DCs and macrophages was found.

Example 3: Preparation and Treatment of mPMs

Mice aged 8-12 wk were injected intraperitoneally with 2 mL each of 3% sterile thioglycolate (BD Biosciences, catalog #211716) medium. The mice were killed 3-5 d later, and cells were harvested by peritoneal lavage with ice-cold RPMI medium containing 2% FBS (FBS) and 1 unit/mL heparin. The cells were pelleted by centrifugation at 500×g for 8 min, washed in ice-cold RPMI containing 2% FBS alone, pelleted by centrifugation, and resuspended in ice-cold Spinner-modification minimum essential medium (SMEM; Sigma, M8167) supplemented with 10% FBS, 2 mM glutamine, and penicillin-streptomycin (SMEM-complete). Cells were then counted, equal numbers were plated into each well of appropriate cell culture dishes, and the cells were then incubated at 37° C. for 2-4 h to allow macrophage adhesion. Contaminating nonadherent cells were then removed by washing culture dishes five times with ice-cold sterile PBS. Fresh SMEM-complete was then added to the plates, which were incubated overnight at 37° C. The following day, the mPMs were treated for 24 h with vehicle, LPS 100 ng/mL, or IL-4 20 ng/mL plus the indicated doses of bryo-1 and then assayed by cytokine ELISA or Western blot.

Example 4: Bryo-1 Attenuates Neurologic Deficits in Established EAE

Figure 2A:
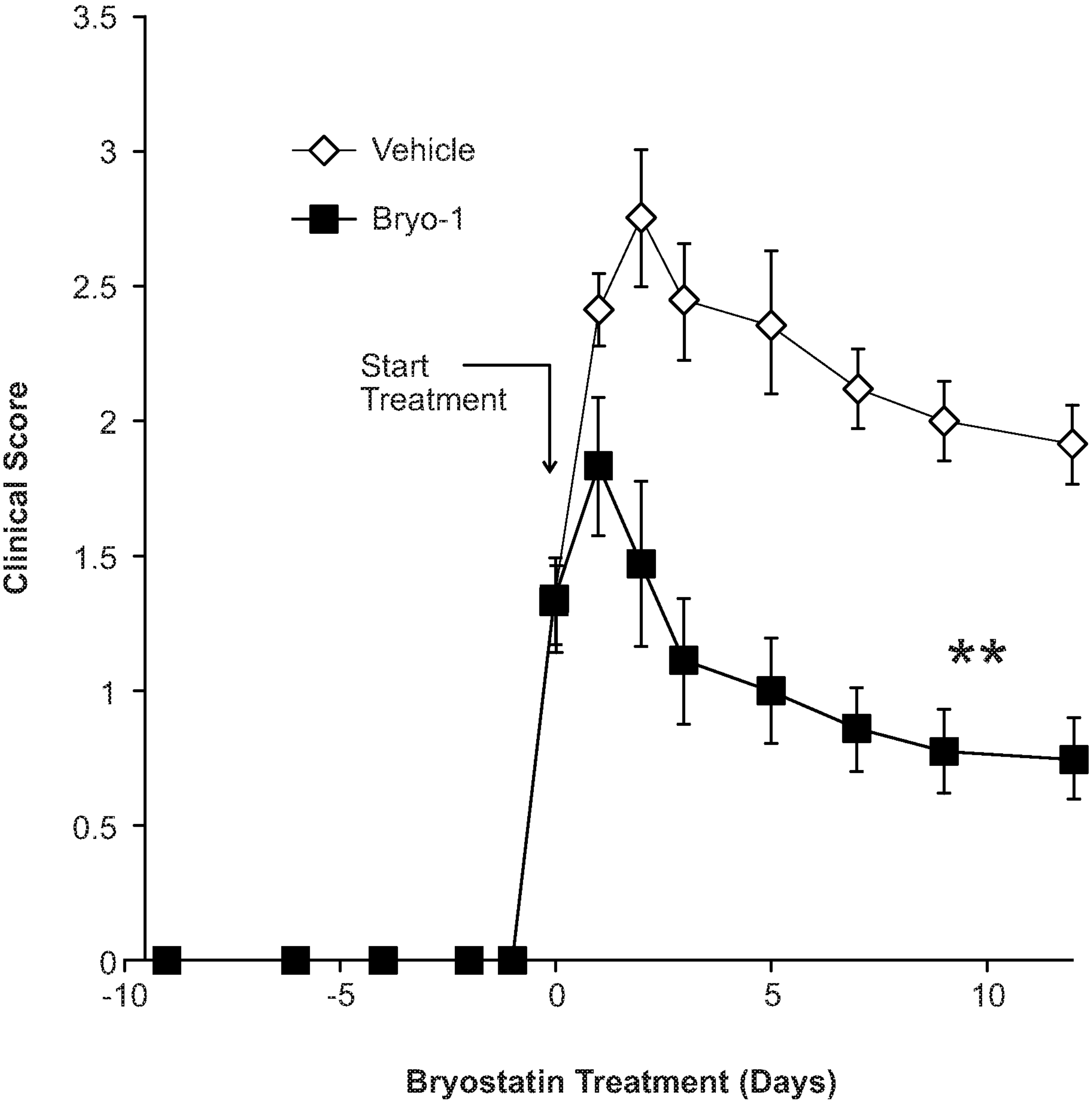
FIG. 2A is a line graph showing EAE mice that were randomized and treatment initiated once they reached a clinical score of 1.0 (tail paralysis); n=9 and 10 mice in vehicle and bryo-1 groups, respectively.

The effects of bryo-1 in two distinct therapeutic paradigms were analyzed. In both paradigms, treatments began after the onset of EAE, but the start of the treatments occurred at two different stages of the disease. In the first set of experiments, mice were randomized and treatment was initiated at the first clinical sign of motor weakness, corresponding to tail paralysis (FIG. 2A).

Figure 2B:
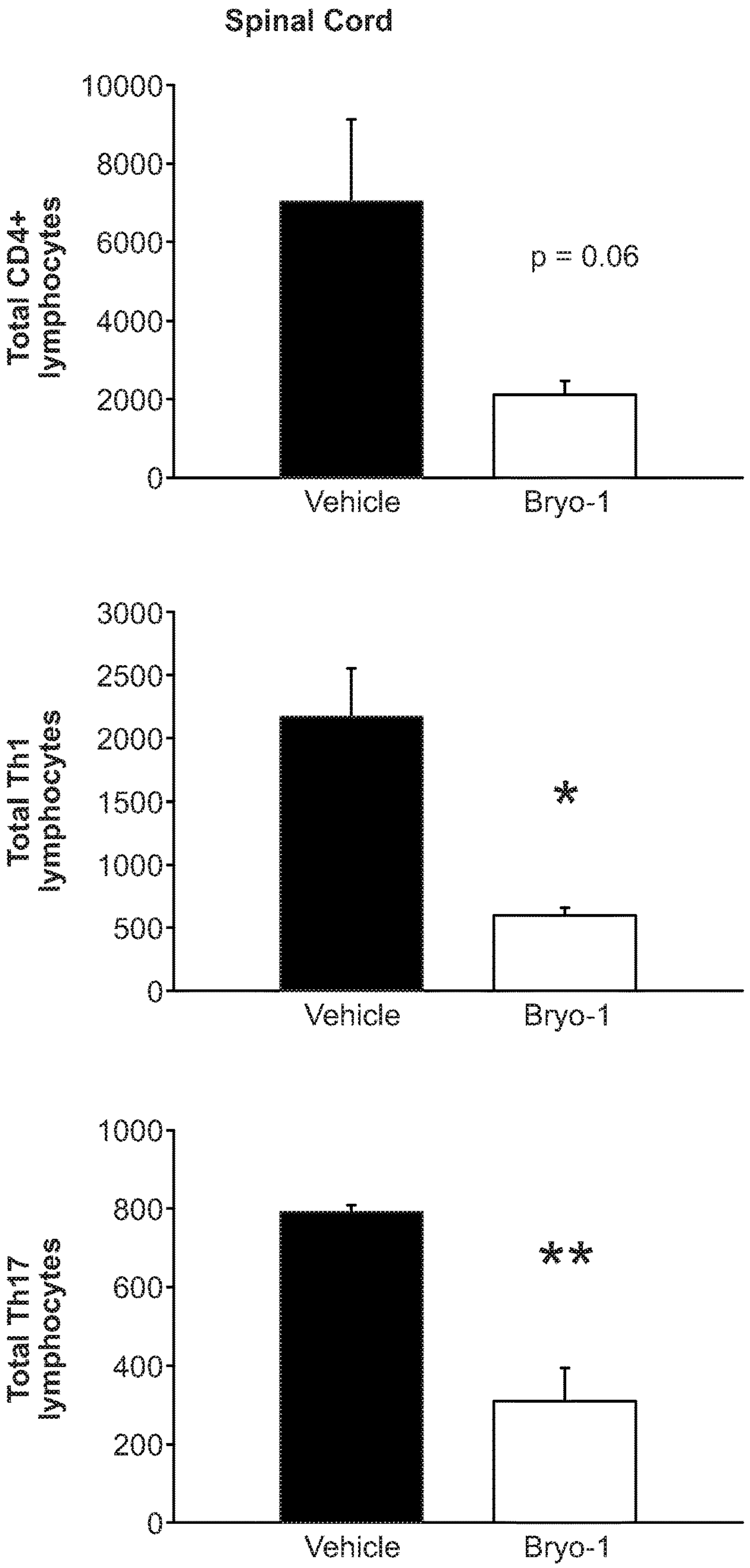
FIG. 2B are bar graphs of the flow cytometry analysis from spinal cord at day 18 post-immunization from EAE mice treated as in FIG. 2A. Data show total numbers of $CD4^+$, Th1, and Th17 lymphocytes; n=4 mice per group.

As shown, bryo-1 substantially attenuated motor deficits and the subsequent course of EAE in this paradigm. Bryo-1-treated mice exhibited a lower peak clinical score and faster recovery than vehicle-treated mice. Flow cytometry from spinal cord at day 18 post-immunization (late peak), several days after initiating treatment, revealed significantly diminished numbers of Th1 and Th17 cells in bryo-1-treated mice, with a near-significant trend (P=0.06) toward decreased total $CD4^+$ lymphocytes, suggesting faster resolution of CNS inflammation (FIG. 2B).

Figure 2C:
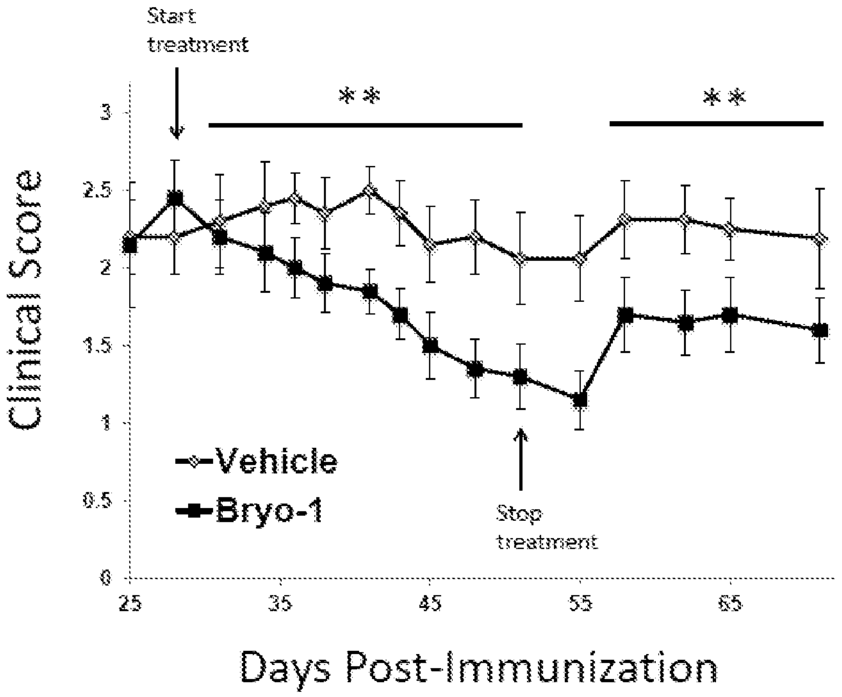
FIG. 2C is a line graph showing EAE mice that were randomized and treatment initiated at day 28 post-immunization. Treatment was discontinued at day 51 post-immunization, and clinical course was followed through day 71; n=5 mice per group. All error bars represent SEM. Statistical significance was determined by Mann-Whitney U test for EAE clinical scoring and by two-tailed Student's t test for flow cytometry data. (C)

In another set of mice, to determine whether bryo-1 could reverse established neurologic deficits in EAE, mice were randomized and began treatment on day 28 post-immunization, more than 10 d after peak disease and once motor deficits had reached a stable plateau (FIG. 2C). Remarkably, bryo-1 reversed motor deficits even at this late stage of disease, with improvement observed within a week of treatment initiation. Treatment was continued for just more than 3 wk and discontinued on day 51 post-immunization. The clinical scores of bryo-1-treated mice steadily improved throughout the treatment period and for several days after discontinuation. Neurologic deficits worsened approximately 1 wk after discontinuing bryo-1, although interestingly, the clinical scores of these mice remained significantly lower than those of the vehicle-treated group.

Although discontinuation of bryo-1 at day 51 of the late-treatment paradigm led to a worsening of motor weakness, the clinical scores of these mice remained below those of vehicle-treated mice (FIG. 2C). In this regard, it was shown that bryo-1 treatment of mPMs inhibits classical activation and augments expression of the M2 marker arginase-1.

Example 5: Bryo-1 Promotes an Anti-Inflammatory Phenotype in APCs and Macrophages To further explore the effects of bryo-1 on APCs, we treated bone marrow-derived DCs (BMDCs) with bryo-1 in vitro, in the presence or absence of proinflammatory stimulation with lipopolysaccharide (LPS; FIG. 3). The effect of bryo-1 on expression of CD40 and CD86 was examined via flow cytometry. CD40 is a costimulatory protein required for proinflammatory activation of APCs, whereas CD86 provides costimulatory activation of T cells upon their binding to APCs. It was observed that bryo-1, even in the absence of LPS, up-regulates CD86, although it has no significant effect on CD40 in the absence of LPS (FIG. 3A). LPS alone markedly increased expression of both CD40 and CD86, but the LPS-induced up-regulation of CD40 was abrogated by simultaneous treatment with bryo-1 at either 20 or 200 nM. Bryo-1 had no effect on CD86 expression in LPS-stimulated BMDCs.

The effects of bryo-1 on cytokine secretion in LPS-stimulated BMDCs was next examined by ELISA (FIG. 3B). Low-dose bryo-1 (10 nM) abrogated LPS-induced secretion of IL-12, a proinflammatory cytokine that promotes Th1 differentiation. In contrast, bryo-1 significantly augmented secretion of IL-10, an anti-inflammatory cytokine that inhibits Th1 differentiation and promotes an immunoregulatory environment.

To explore the effects of bryo-1 on myeloid cells of the innate immune system, murine peritoneal macrophages (mPMs) was utilized. Similar to its effect on dendritic cells, low-dose bryo-1 inhibited LPS-induced secretion of IL-12 and another proinflammatory cytokine, IL-6 (FIG. 3C). Furthermore, bryo-1 treatment of mPMs potentiated the IL-4-induced expression of arginase-1, a marker of the anti-inflammatory and repair-promoting M2 macrophage phenotype (FIG. 3D).

Example 6: Direct Effects of Bryo-1 on T Cells

Bryo-1 was then evaluated to determine its direct influences on $CD4^+$ T cells in vitro that might be relevant to its observed benefit in EAE (FIG. 4). Although direct effects were observed in naive $CD4^+$ lymphocytes stimulated with α-CD3/CD28 antibodies, these effects were in general more modest than those observed in DCs, required higher doses of bryo-1, and were seen only with low levels of T-cell stimulation. Thus, bryo-1 treatment inhibited up-regulation of CD44 (a marker of T-cell activation; FIG. 4A) and IFNγ (FIG. 4B) and increased expression of the regulatory T-cell marker FoxP3 (FIG. 4C), but only at a dose of 200 nM in cells stimulated with 0.25 μg/mL of α-CD3 and α-CD28 antibodies. With stronger T-cell stimulation (1 m/mL of α-CD3/CD28), these effects were lost.

Example 7: Bryo-1 Promotes Generation of Oligodendrocyte-Lineage Cells from Neural Stem Cells We examined the effect of bryo-1 on neurospheres, which are neural stem cell-like cells. Treatment of neurospheres with 20 nM bryo-1, given every other day for 1 week, led to increased expression of the oligodendrocyte marker 04. Results are shown in FIG. 5 where left panel shows cultured neurospheres cultured with vehicle only (control), and right panel shows a representative image where cultured neurospheres were treated with 20 nM bryo-1 on alternating days for 1 week.

Example 8: Bryo-1 Promotes a Regenerative Anti-Inflammatory M2 Phenotype in Cultured Glial Cells Mixed glial cultures (MGCs) obtained from the cerebral cortices of P1-P3 neonatal C57BL/6J mice were used, prepared as described by Saura et al., Glia (2003) 44:183-189. Mixed glial cultures were treated with LPS (FIG. 6A) or IL4 (FIG. 6B) ±vehicle or the indicated dose of bryo-1. Expression of iNOS or Argl, respectively, was assessed by immunoblot. Images are representative of 3 independent experiments. Bryo-1 blocked the induction of iNOS (an M1 marker) by LPS in MGCs (FIG. 6A). Conversely, bryo-1 treatment of MGCs at a dose as low as 1 nM dramatically augmented expression of Argl, a marker of the reparative anti-inflammatory M2 phenotype (FIG. 6B).

Example 9: Bryo-1 Treatment Increases the Rate of Remyelination after Cuprizone-Induced Demyelination Cuprizone-induced demyelination was elicited as described by Baxi et al., Glia (2017) 65:2087-098, with minor modification. Female C57BL/6J mice (8 weeks old) were fed 0.2% cuprizone for 5 weeks to induce demyelination of the corpus callosum and then returned to normal feed. The mice (n=2 per group) were then treated with either bryo-1 (30 μg/kg) or vehicle by IP injection every other day beginning on the first day of re-feeding with normal feed, and the extent of corpus callosum remyelination was assessed by Black-Gold II myelin staining on day 8 after re-feeding. Bryo-1 treatment increased the rate of remyelination as measured by the extent of Black-Gold II staining (FIG. 7).

Example 10: Bryo-1 Promotes Remyelination in Lysolecithin-Induced Demyelination Model To evaluate the impact of systemic treatment with bryo-1 on physiologic demyelination in vivo, we conducted a lysolecithin (LPC)-induced demyelination animal study. LPC was stereotactically injected into the corpus callosum of 12-week old C57BL/6J mice. Bryo-1 (30 μg/kg) or vehicle was injected IP at 3, 5, 7, and 9 dpl followed by immunofluorescent assessment of MBP expression at 10 dpl. Bryo-1 appears to have increased the rate of oligodendrogenesis, as assessed by MBP staining (FIG. 10).

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document, including Kornberg et al., "Bryostatin-1 Alleviates Experimental Multiple Sclerosis," PNAS, 115(9):2186-2191, Feb. 27, 2018, are hereby incorporated herein by reference, each in its entirety, for all purposes.

What is claimed is:

1. A method for treating multiple sclerosis in patient, comprising:

a) identifying a patent suffering from relapsing-remitting MS, secondary-progressive MS, primary-progressive MS, or progressive-relapsing MS b) administering a therapeutically effective amount of a bryostatin to the identified patient, thereby treating the patient for relapsing-remitting MS, secondary-progressive MS, primary-progressive MS, or progressive-relapsing MS.

2. The method of claim 1, wherein the bryostatin is bryostatin-1 of the structure:

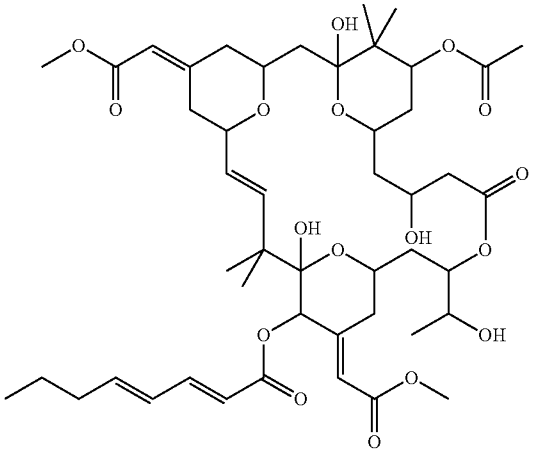

(bryostatin-1)

or a derivative, salt, or prodrug thereof.

3. The method of claim 1, wherein the bryostatin is bryostatin-1 of the structure:

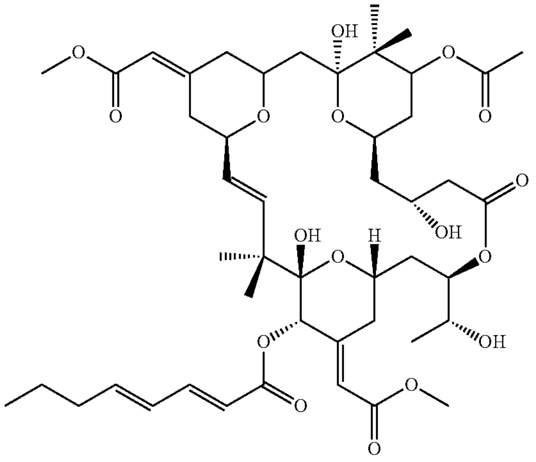

(bryostatin-1)

or a derivative, salt, or prodrug thereof.

4. The method of claim 1, wherein the bryostatin derivative is:
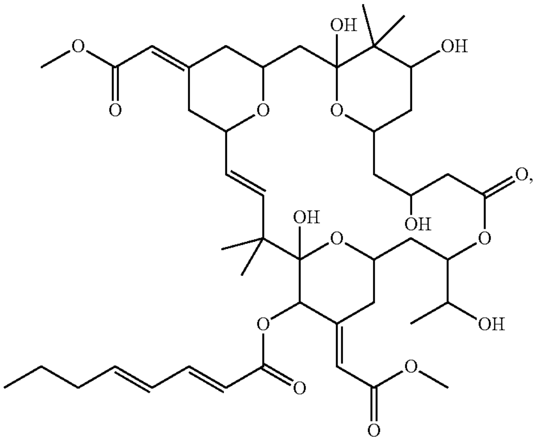
,
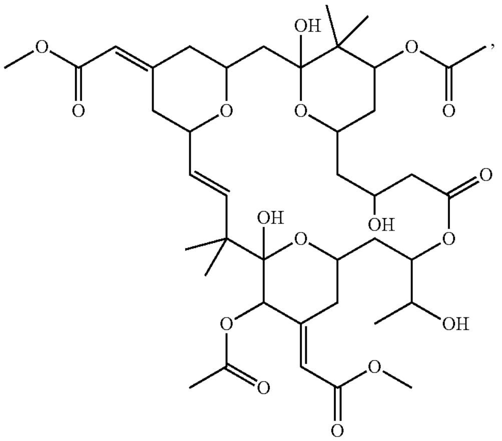
,
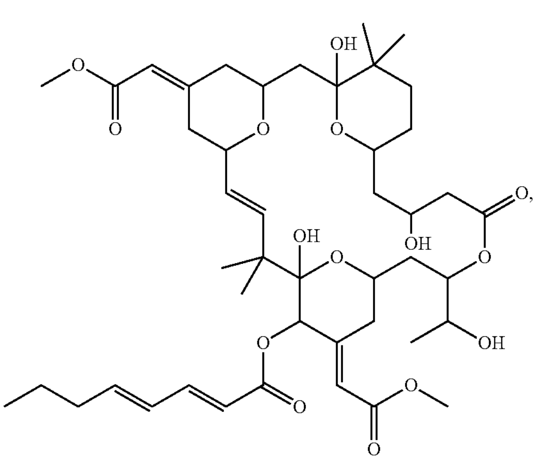
,
-continued
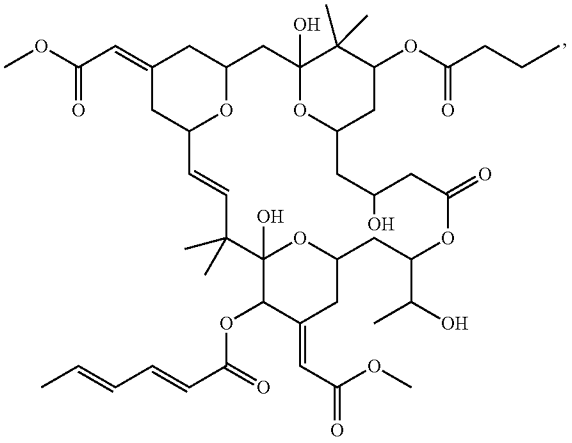
,
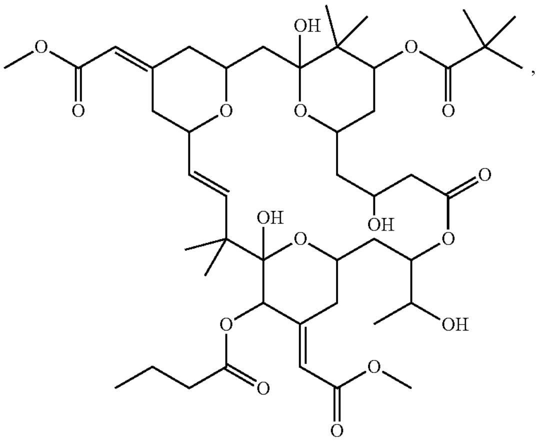
,
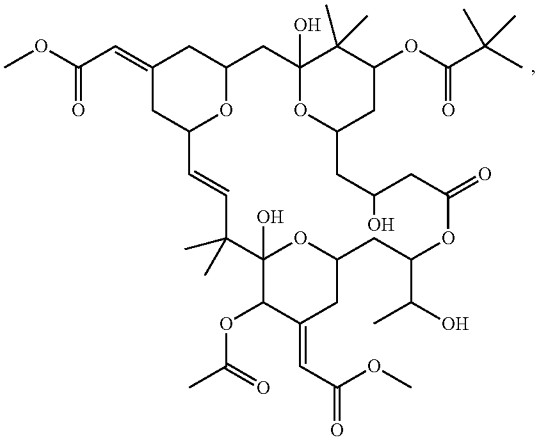
, -continued
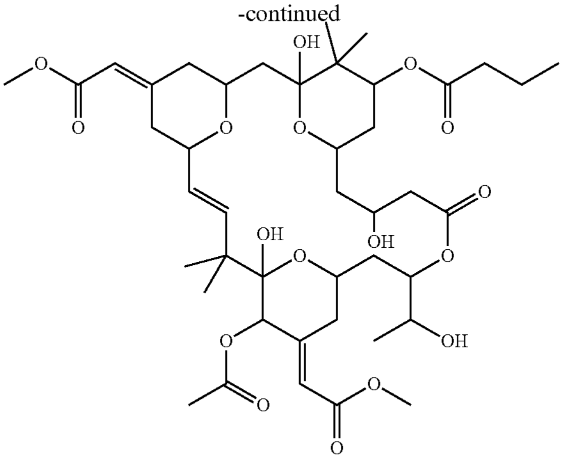
,
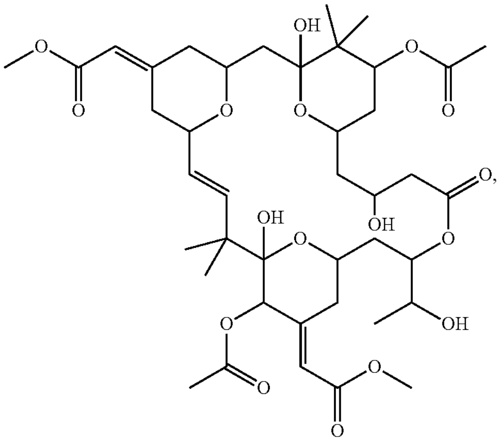
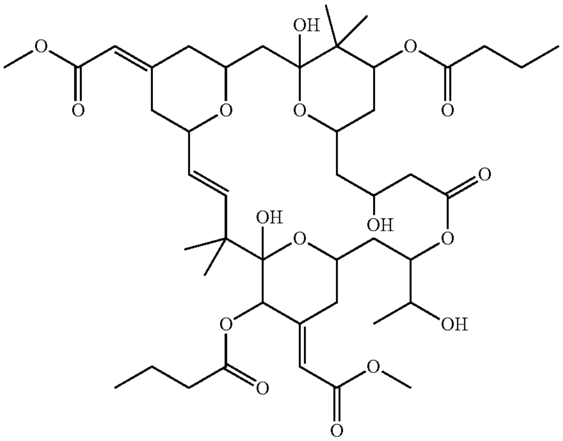
,
-continued
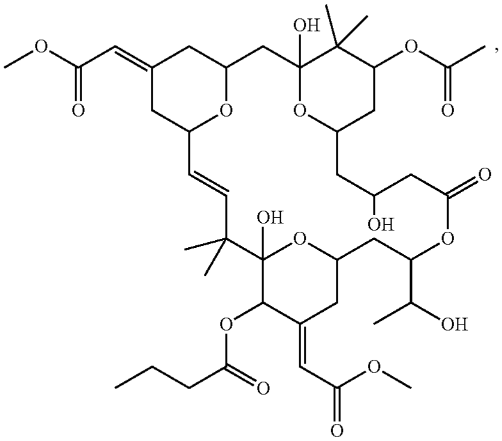
,
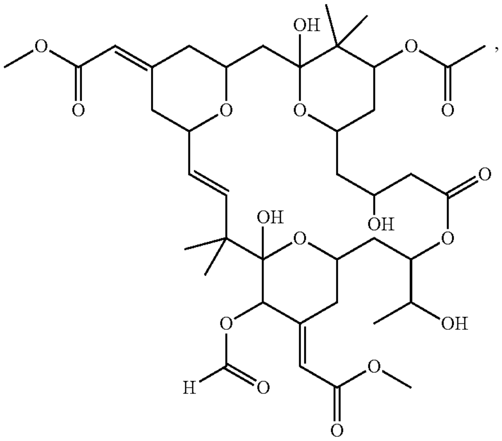
,
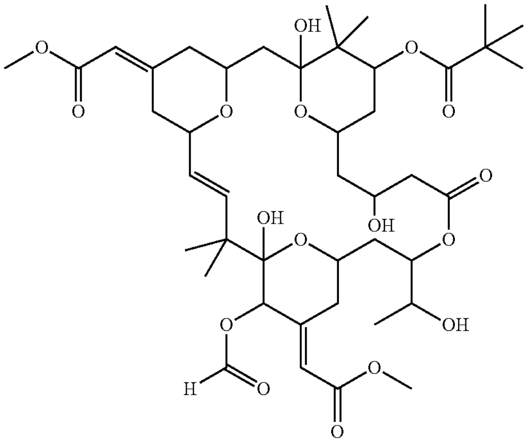
,
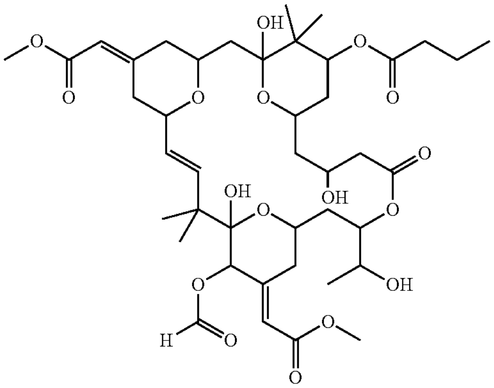
, or -continued

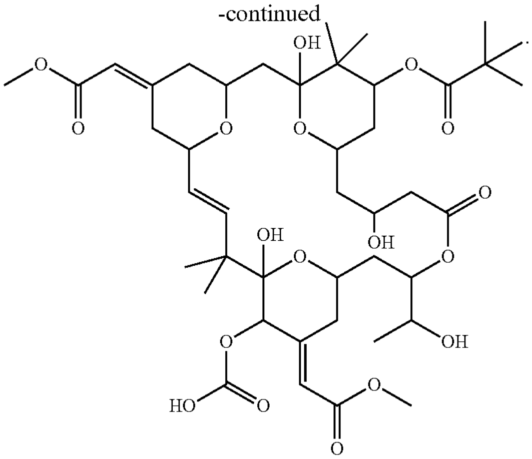

5. The method of claim 1, further comprising administering another agent effective for treating multiple sclerosis.

6. The method of claim 1 wherein the patient is a human.

7. The method of claim 1 wherein the patient is identified as suffering from relapsing-remitting MS and the bryostatin is administered to the identified patient.

8. The method of claim 1 wherein the patient is identified as suffering from secondary-progressive MS and the bryostatin is administered to the identified patient.

9. The method of claim 1 wherein the patient is identified as suffering from primary-progressive MS and the bryostatin is administered to the identified patient.

10. The method of claim 1 wherein the patient is identified as suffering from progressive-relapsing MS and the bryostatin is administered to the identified patient.

* * * * *